(12) United States Patent
Ohnogi et al.

(10) Patent No.: US 7,268,160 B2
(45) Date of Patent: Sep. 11, 2007

(54) REMEDIES

(75) Inventors: Hiromu Ohnogi, Muko (JP); Masahiro Shiraga, Otsu (JP); Eiji Kobayashi, Otsu (JP); Tuo-Ping Li, Otsu (JP); Suzu Deguchi, Otsu (JP); Eiji Nishiyama, Moriyama (JP); Hiroaki Sagawa, Kusatsu (JP); Ikunoshin Kato, Uji (JP)

(73) Assignee: Takara Bio, Inc., Shiga (JP)

( * ) Notice: Subject to any disclaimer, the term of this patent is extended or adjusted under 35 U.S.C. 154(b) by 86 days.

(21) Appl. No.: 10/182,193

(22) PCT Filed: Jan. 26, 2001

(86) PCT No.: PCT/JP01/00513

§ 371 (c)(1),
(2), (4) Date: Jul. 26, 2002

(87) PCT Pub. No.: WO01/54682

PCT Pub. Date: Aug. 2, 2001

(65) Prior Publication Data

US 2003/0144316 A1    Jul. 31, 2003

(30) Foreign Application Priority Data

Jan. 27, 2000 (JP) ............... 2000-019208
Jan. 27, 2000 (JP) ............... 2000-019331
Aug. 24, 2000 (JP) ............... 2000-254683
Oct. 6, 2000 (JP) ............... 2000-308519

(51) Int. Cl.
*A61K 31/35* (2006.01)
*A61K 31/22* (2006.01)
*C07D 307/02* (2006.01)
*C07C 67/02* (2006.01)

(52) U.S. Cl. ............... 514/460; 514/546; 549/502; 560/255

(58) Field of Classification Search ............... 560/255; 568/308, 326, 331
See application file for complete search history.

(56) References Cited

U.S. PATENT DOCUMENTS

| 3,761,471 A | * | 9/1973 | Nishimura et al. ......... 564/228 |
| 5,059,627 A | | 10/1991 | Goto et al. |
| 5,106,871 A | | 4/1992 | Komazawa et al. |
| 5,234,951 A | | 8/1993 | Komazawa et al. |
| 5,679,716 A | | 10/1997 | Tobe et al. |
| 5,928,654 A | | 7/1999 | Duranton |

FOREIGN PATENT DOCUMENTS

| EP | 0 261 977 A2 | 3/1988 |
| EP | 0 998 939 A1 | 5/2000 |
| EP | 1 175 907 A1 | 1/2002 |
| JP | 1-42422 A | 2/1989 |
| JP | 1042422 A | 2/1989 |
| JP | 1-125320 A | 5/1989 |
| JP | 1-125320 A | 5/1989 |
| JP | 2-104568 A | 4/1990 |
| JP | 2-187765 A | 7/1990 |
| JP | 2-187765 A | 7/1990 |
| JP | 3-122645 A | 5/1991 |
| JP | 3-122645 A | 5/1991 |
| JP | 5-61220 A | 3/1993 |
| JP | 5-061220 A | 3/1993 |
| JP | 5-78384 A | 3/1993 |
| JP | 5-078384 A | 3/1993 |
| JP | 05-246932 | * | 9/1993 |
| JP | 5-246932 A | 9/1993 |
| JP | 5-246932 A | 9/1993 |
| JP | 07194355 | * | 8/1995 |
| JP | 95-110812 B2 | 11/1995 |
| JP | 8-027086 A | 1/1996 |
| JP | 2-719042 B2 | 2/1998 |
| JP | 10114649 A | 5/1998 |
| JP | 11246398 A | 9/1999 |
| WO | WO98/58913 A1 | 12/1998 |
| WO | WO 00/48586 A1 | 8/2000 |
| WO | WO 01/30335 A2 | 5/2001 |

OTHER PUBLICATIONS

Yabe et al, Phytomedicine, Enhancements of Choline Acetyltransferase Activity and Nerve Growth Factor Secretion by Polygalae Radix-Extract, 1997, 4(3), pp. 199-205. Abstract only.*

(Continued)

*Primary Examiner*—Paul A. Zucker
(74) *Attorney, Agent, or Firm*—Birch, Stewart, Kolasch & Birch, LLP

(57) ABSTRACT

The present invention provides a therapeutic agent or prophylactic agent for a disease that requires enhancement of nerve growth factor production, an enhancer for nerve growth factor production, or a food, beverage or feed for enhancing nerve growth factor production, each comprising as an effective ingredient a specified compound or a salt thereof having enhancing activity for nerve growth factor production; a method for enhancing nerve growth factor production, comprising administering to a mammal the above-mentioned compound or a salt thereof; and use of the above-mentioned compound or a salt thereof in the preparation of a therapeutic agent or prophylactic agent for a disease that requires enhancement of nerve growth factor production, an enhancer for nerve growth factor production, or a food, beverage or feed for enhancing nerve growth factor production. In addition, the present invention provides novel compounds having enhancing activity for nerve growth factor production.

9 Claims, 9 Drawing Sheets

OTHER PUBLICATIONS

Kourounakis et al., Pharm. Res., vol. 12, No. 8, pp. 1199-1204 (1995).

Angeliki Kourounakis et al., *Pharmaceutical Research*, vol. 12, No. 8, (1995), pp. 1199-1204.

Robert D. Terry et al., *Ann. Rev. Neurosci.*, vol. 3, (1980), pp. 77-95.

S. Korsching et al., *The EMBO Journal*, vol. 4, No. 6, (1985), pp. 1389-1393.

Jean L. Marx, *Science*, vol. 232, (1986), pp. 1341-1342.

Franz Hefti, *The Journal of Neuroscience*, vol. 6, No. 8, (Aug. 1986), pp. 2155-2162.

F. Hefti et al., *Brain Research*, vol. 293, (1984), pp. 305-311.

Lawrence F. Kromer, *Science*, vol. 235, (1987), pp. 214-216.

Lawrence R. Williams et al., *Proc. Natl. Acad. Sci.*, vol. 83, (Dec. 1986), pp. 9231-9235.

Sramek J J et al.: Drugs and Aging, ADIS International Ltd, vol. 14, No. 5 (1999) pages 359-373, XP000901933 (abstract).

Yoshiko Furukawa et al., *The Journal of Biological Chemistry*, vol. 259, No. 2, (Jan. 25, 1984), pp. 1259-1264.

Shoei Furukawa et al., *Biochemical and Biophysical Research Communications*, vol. 136, No. 1, (Apr. 14, 1986), pp. 57-63.

Yoshiko Furukawa et al., *The Journal of Biological Chemistry*, vol. 261, No. 13, (May 5, 1986), pp. 6039-6047.

\* cited by examiner

REMEDIES

This application is the national phase under 35 U.S.C. § 371 of PCT International Application No. PCT/JP01/00513 which has an International filing date of Jan. 26, 2001, which designated the United States of America.

TECHNICAL FIELD

The present invention relates to a medicament, a reagent, a food, beverage or feed, each having enhancing action for nerve growth factor production.

BACKGROUND ART

Nerve cells play a principal role for sustaining psycho-activities of human beings such as intellectual functions, memory, emotions and behaviors. It has been thought that the differentiation, survival and exhibition of functions of the nerve cells which are the foundations of these psycho-activities need a neurotrophic factor specific for each nerve cell. Among the neurotrophic factors, one of which existence and function have been firstly elucidated is a nerve growth factor (hereinafter simply referred to as "NGF"), and currently, there have been found a brain-derived-neurotrophic factor, neurotrophin-3, neurotrophin-4/5, and the like.

NGF is a neurotrophic factor of a large cellular cholinergic nerve cell of basal portion of the forebrain, so that its association with Alzheimer's dementia has been remarked [*Pharmacia*, Vol. 22 No. 2, 147-151 (1986), *Ronen Seishin Jgaku* (Senile Psychiatry), Vol. 3 No. 6, 751-758 (1986)].

Alzheimer's dementia refers to a disease that gives a pathological finding such as senile plaque or Alzheimer's fibrillar changes, which are accompanied by a clinical picture such as developmental disability, manic state, tonic seizures of lower limbs, or epileptic seizure, and is one disease of senile dementia. The Alzheimer's dementia tends to be increasing in recent aging society, so that a larger societal interest has been drawn thereto. However, there has not yet been found a method for ameliorating or treating such symptoms.

In the brain of a patient with Alzheimer's dementia, there has been found a dramatic denaturation, a drastic lowering of the activity of choline acetyl transferase (CAT), in the basal portion of the forebrain centering about Meynert's basal nuclei [*Annu. Rev. Neurosci.*, Vol. 3, 77 (1980)]. In the studies of a rat brain in 1985, there has been elucidated that NGF is a neurotrophic factor at this site of the brain [*EMBO J.*, Vol. 4, 1389 (1985)], so that the association of NGF with this disease has been remarked. In addition, there have been elucidated that in the striate body of the brain of a patient with Huntington's chorea, there are remarkable detachment of GABAergic nerve cell as well as detachment of cholinergic nerve cell, so that NGF also acts on the endogenous cholinergic nerve cell of the striate body [*Science*, Vol. 234, 1341 (1986)], addressing a possibility that this disease is associated with NGF. The effects of NGF have been studied with an animal such as a rat which can serve as a model for various nerve diseases. There has been reported that the degeneration of the nerve cell can be stopped in a rat if NGF is intracerebrally administered before the degeneration becomes remarkable, and that the lowering of CAT activity is also prevented [*J. Neurosci.*, Vol. 6, 2155 (1986), *Brain Res.*, Vol. 293, 305 (1985), *Science*, Vol. 235, 214 (1986), *Proc. Natl. Acad. Sci. USA*, Vol. 83, 9231 (1986)]. Also, it has been proven that NGF is biosynthesized in the peripheral sympathetic nerve-dominant tissues and in the brain, and that each of fibroblasts or astroglia which are interstitial cells for peripheral tissues or brain tissues plays an important role for the NGF biosynthesis [*J. Bol. Chem.*, Vol. 259, 1259 (1984), *Biochem. Biophys. Res. Commun.*, Vol. 136, 57 (1986)]. In addition, it has been elucidated that antigenicity, molecular weight, isoelectric point and biological activity of the fibroblast-producing or astroglia-producing NGF are the same as NGF of conventionally well studied submandibular gland. At the same time, it has been found that a catecholamine such as norepinephrine, epinephrine or dopamine shows enhancing action for NGF production by a test of adding various neurotransmitters to a culture medium of fibroblasts (L-M cells) and astroglia [*J. Biol. Chem.*, Vol. 201, 6039 (1986)].

There has been expectation that NGF can be used as a therapeutic agent for stopping degeneration in a nerve disease in which a site at which NGF acts as a neurotrophic factor is degenerated. In addition, once the cranial nerve cells are degenerated by cebrovascular disorders, cerebral tumor, cerebral apicitus, degenerative disease of head injury, intoxication with an anesthetic, or the like, the degenerated cranial nerve cells would never recover during the life time, whereby various disorders such as emotional disorders and behavioral abnormality are consequently caused in addition to lowering in the intellectual functions and memory disabilities. On the other hand, nerve fiber shows plasticity, that is, when the nerve fiber is damaged, budding takes place from its surrounding healthy fibers, so that a new synapsis is formed in place of the damaged synapsis. Therefore, it has been expected that NGF can be used as a therapeutic agent for promoting restoration and regeneration of nerve functions at this stage.

However, when NGF is applied to a treatment of various nerve diseases, NGF must reach in very close vicinity of nerve cell that requires NGF, and NGF must be transmitted to lesion site of the cranial cell in a case of a disease in the central nervous system. However, NGF cannot be transmitted into the brain through the blood system. This is because the vascular endothelial cells in the brain are bound to each other by adhesion bonding (referred to as brain blood barrier), so that there is a limitation in the transport of a substance other than water, gas or an oil-soluble substance from blood to a brain tissue, whereby a protein (including NGF), which is polymeric substance, cannot pass through the brain blood barrier. There is too large a risk involved in the introduction of NGF directly into the brain by a surgical means, even if the introduction is conducted by the current techniques.

On the other hand, there has been developed a substance for enhancing NGF production, not a direct administration of NGF. Besides the above-mentioned catecholamines, there has been known a substance showing enhancing action for NGF production, such as caffeic acid, or a catechol in which a substituent is introduced into 4-position, including, for instance, as a representative compound, 4-methyl catechol (Japanese Examined Patent Publication No. Hei 5-29207).

Also, Japanese Patent Laid-Open No. Hei 2-104568, Japanese Patent Gazette No. 2719042, Japanese Patent Laid-Open No. Hei 8-27086, and Japanese Examined Patent Publication No. Hei 7-110812 each discloses a compound having enhancing activity for NGF production. Most of the compounds, however, have various problems such that the compounds are substances having strong toxicity such as those showing acute toxicity, substances having effective concentration very closely approximating concentration at which toxicity is shown, or substances exhibiting severe adverse actions against the nervous system such as nerve excitation action (for instance, the above-mentioned catecholamine has been known as a representative adrenergic agent), that a concentration range effective for enhancing activity for NGF production is narrow, and that control of dose is difficult. For instance, as to a substance disclosed in Japanese Examined Patent Publication No. Hei 7-110812, there is exhibited twin-peak property between the enhancing activity for NGF production and the compound concentration, so that its control of the dose is difficult to be used as a medicament. In addition, the concentration at which the enhancing activity for NGF production is confirmed for the compounds is disclosed in Japanese Patent Laid-Open No. Hei 2-104568, Japanese Patent Gazette No. 2719042, and Japanese Patent Laid-Open No. Hei 8-27086 is each only one point, so that a concentration range effective for the activity remains unknown. There are various problems as described above, and substances showing enhancing action for NGF production have not yet been actually used.

DISCLOSURE OF INVENTION

As the result of intensive studies, the present inventors have found that the compound represented by the following general formula (1) has the features of 1) having a stronger enhancing activity at a low concentration, 2) having a wider concentration region showing enhancing activity, and/or 3) having lower toxicity, as compared to a known compound having enhancing action for NGF production, and the present inventor has been perfected thereby.

Summarizing the present invention, the present invention relates to:

[1] a therapeutic agent or prophylactic agent for a disease that requires enhancement of nerve growth factor production, characterized in that the therapeutic agent or prophylactic agent comprises as an effective ingredient at least one compound selected from the group consisting of a compound represented by the following general formula (1):

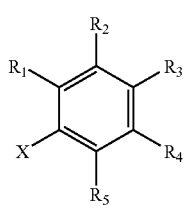

(1)

wherein each of $R_1$, $R_2$, $R_3$, $R_4$ and $R_5$, which may be identical or different, is hydrogen atom, hydroxyl group, an alkoxy group or an acyloxy group; X is a group represented by the following general formula (2):

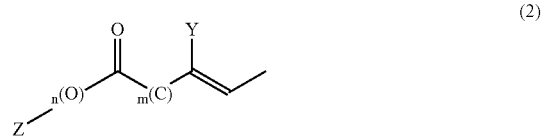

(2)

wherein Z is hydrogen atom or an aliphatic group, an aromatic group or an aromatic-aliphatic group, wherein a characteristic group may be introduced into the aliphatic group, the aromatic group or the aromatic-aliphatic group; Y is hydrogen atom or hydroxyl group; and each of m and n is 0 or 1; a group represented by the following general formula (3):

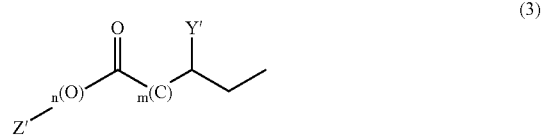

(3)

wherein Z' is hydrogen atom or an aliphatic group, an aromatic group or an aromatic-aliphatic group, wherein a characteristic group may be introduced into the aliphatic group, the aromatic group or the aromatic-aliphatic group; Y' is hydrogen atom or hydroxyl group; and each of m and n is 0 or 1; or a group represented by the following general formula (4):

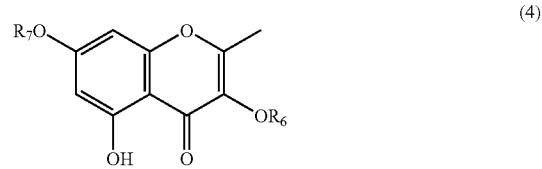

(4)

wherein each of $R_6$ and $R_7$, which may be identical or different, is hydrogen atom, a sugar residue, or an aliphatic group, an aromatic group or an aromatic-aliphatic group, wherein a characteristic group may be introduced into the aliphatic group, the aromatic group or the aromatic-aliphatic group, excluding a case where $R_1$, $R_4$ and $R_5$ are all hydrogen atoms, $R_2$ and $R_3$ are all hydroxyl groups, and X is represented by the general formula (2) in the general formula (1), wherein n is 1, m is 0, and Z and Y are hydrogen atom in the general formula (2), and pharmacologically acceptable salts thereof;

[2] an enhancer for nerve growth factor production, characterized in that the enhancer comprises as an effective ingredient at least one compound selected from the group consisting of the compound represented by the general formula (1) and pharmacologically acceptable salts thereof as defined in item [1] above;

[3] a method for enhancing nerve growth factor production, characterized by administering to an animal at least one compound selected from the group consisting of the compound represented by the general formula (1) and pharmacologically acceptable salts thereof as defined in item [1] above;

[4] a food, beverage or feed for enhancing nerve growth factor production, characterized in that the food, beverage or feed comprises as an effective ingredient at least one compound selected from the group consisting of the compound represented by the general formula (1) and pharmacologically acceptable salts thereof as defined in item [1] above;

[5] use of at least one compound selected from the group consisting of the compound represented by the general formula (1) and pharmacologically acceptable salts thereof as defined in item [1] above in the preparation of a therapeutic agent or prophylactic agent for a disease that requires enhancement of nerve growth factor production, an enhancer for nerve growth factor production, or a food, beverage or feed for enhancing nerve growth factor production; and

[6] a compound selected from the group consisting of the compounds represented by the following formulas (5) to (12):

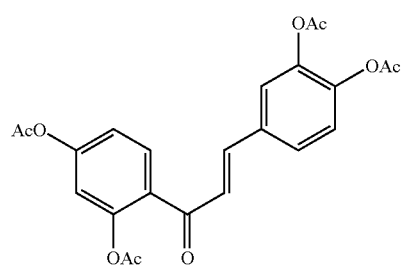
(5)

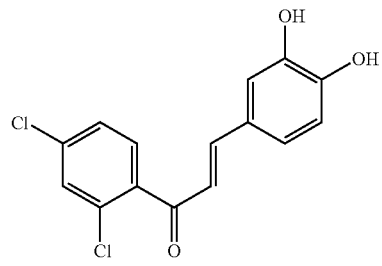
(6)

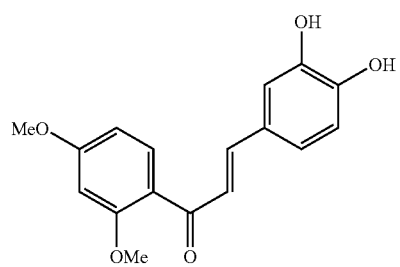
(7)

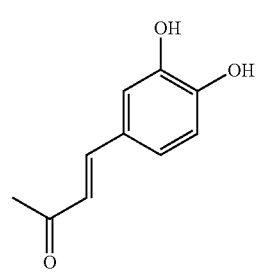
(8)

-continued

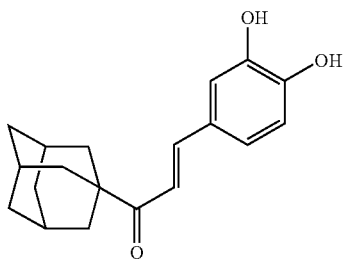
(9)

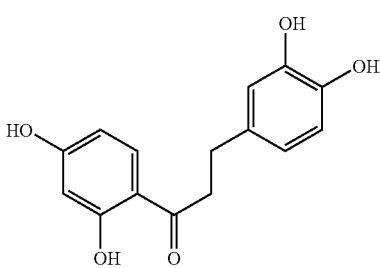
(10)

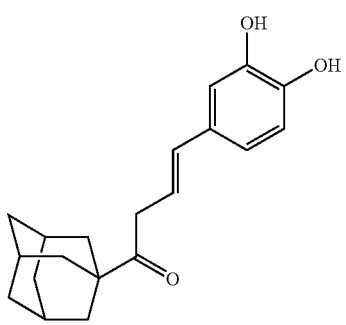
(11)

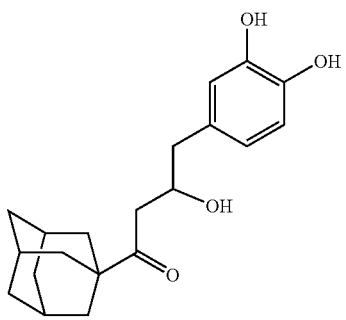
(12)

BEST MODE FOR CARRYING OUT THE INVENTION

Figure 1:
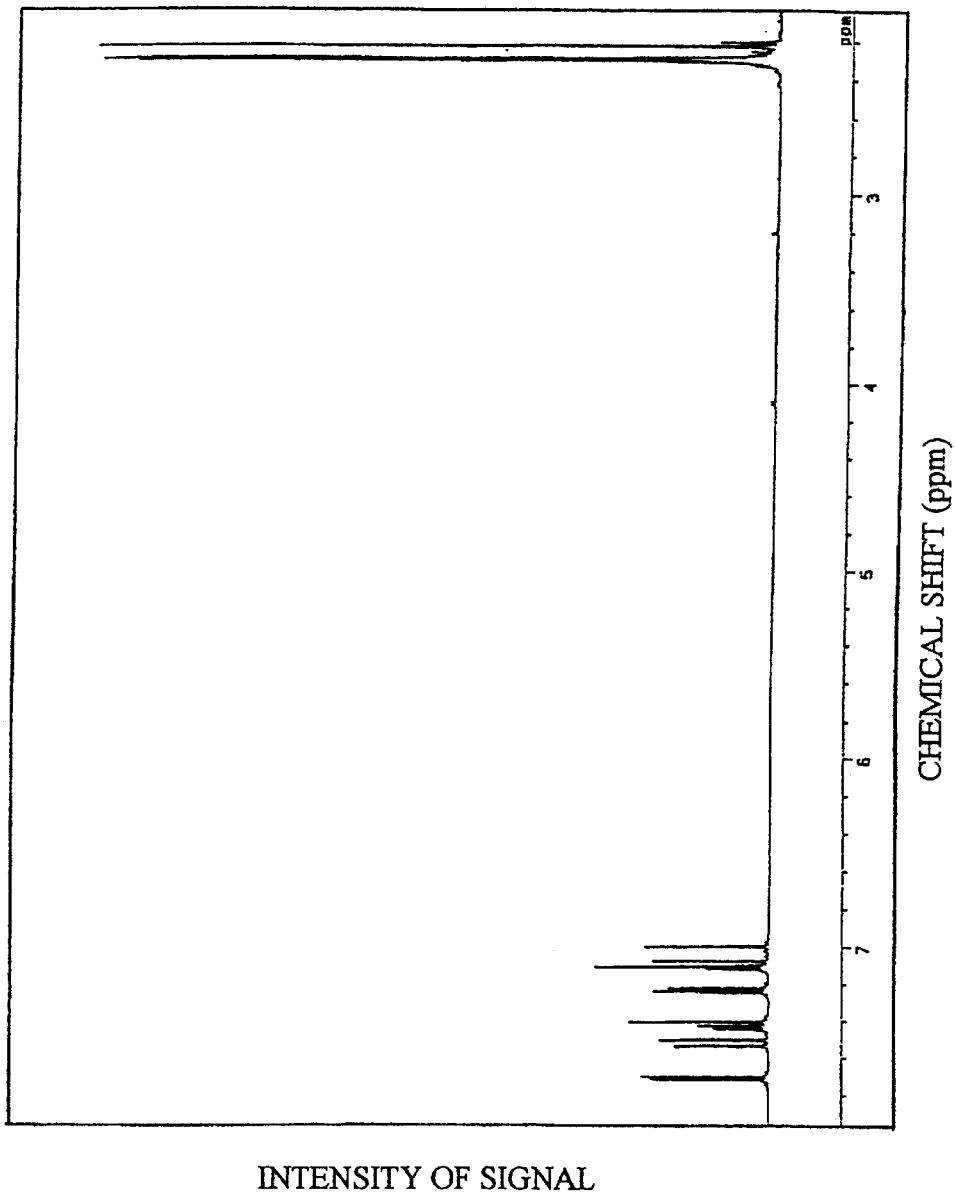
FIG. 1 is a graph showing $^1$H-NMR spectrum of a compound (5).

The compound used as an effective ingredient in the present invention is at least one compound selected from the group consisting of the compound represented by the above-mentioned general formula (1) and a salt thereof, and is not particularly limited, as long as the compound has enhancing action for NGF production. The salt is preferably a pharmacologically acceptable salt. In addition, as described below, the compound represented by the above-mentioned general formula (1) may be a derivative of the compound which is capable of functioning as a prodrug. Therefore, the effective ingredient according to the present invention encompasses the compound represented by the above-mentioned general formula (1) and a salt thereof, and a derivative of the compound represented by the above-mentioned general formula (1) and a salt thereof as long as the desired effects of the present invention can be obtained.

In the present specification, the term "enhancing activity for NGF production" and "enhancing action for NGF production" each refers to a function for enhancing NGF production and enhancement of NGF production, and is not intended to particularly strictly distinguish in its meaning. In addition, the term "enhance" encompasses an embodiment in which the amount of the desired substance is increased after the action as compared to that before the action of the effective ingredient according to the present invention, as well as an embodiment in which the desired substance is produced by the action of the effective ingredient according to the present invention (induce).

Preferred examples of the compound represented by the above-mentioned general formula (1) used as the effective ingredient include a compound having a 3-phenyl-2-propen-1-one bone structure, a compound having a 3-phenylpropan-1-one bone structure, a compound having a 4-phenyl-3-buten-1-one bone structure, a compound having a 4-phenylbutan-1-one bone structure, and the like. In the present specification, the structure of the compound having a 3-phenyl-2-propen-1-one bone structure or a 4-phenyl-3-buten-1-one bone structure, for instance, the compound shown in the above-mentioned formula (5) or formula (11) is shown as a trans form with regard to the steric conformation of its double bond site. However, the compound used in the present invention is not particularly limited to trans form, and the compound may take a cis form, as long as the compound has enhancing activity for NGF production. In addition, other various isomers such as optical isomers, keto-enol tautomers, and geometric isomers of the compound represented by the above-mentioned general formula (1) can be all used in the present invention, as long as they have enhancing activity for NGF production. Further, each of isomers can be used as an isolated form or as its mixtures.

Each substituent in the above-mentioned general formulas (1) to (4) will be described. In the present specification, an alkoxy group can be represented by $R_iO\text{---}$. Here, $R_i$ includes a linear alkyl group having 1 to 30 carbon atoms such as methyl group, ethyl group, and n-propyl group; a branched alkyl group such as isopropyl group, isobutyl group, sec-butyl group, tert-butyl group, isopentyl group, neopentyl group, and tert-pentyl group; a linear alkenyl group such as ethenyl group, allyl group, trans-1-propenyl group, cis-1-propenyl group, cis-8-heptadecenyl group, cis-8-cis-11-heptadecadienyl group, cis-8-cis-11-cis-14-heptadecatrienyl group, cis-5-cis-8-cis-11-heptadecatrienyl group, cis-4-cis-7-cis-10-nonadecatrienyl group, cis-4-cis-7-cis-10-cis-13-nonadecatetraenyl group, cis-4-cis-7-cis-10-cis-13-cis-16-nonadecaheptaenyl group, cis-12-heneicosenyl group, and cis-3-cis-6-cis-9-cis-12-cis-15-cis-18-heneicosahexaenyl group; a branched alkenyl group such as isopropenyl group, cis-1-methyl-1-propenyl group, trans-1-methyl-1-propenyl group, trans-1-methyl-1-propenyl group, and trans-1-ethyl-1-propenyl group; aromatic groups given below; and the like. From the viewpoint of the exhibition of the desired effects of the present invention, the preferred examples of the alkoxy group include methoxy group, ethoxy group, allyloxy group, phenoxy group, and the like.

In addition, in the present specification, the acyloxy group can be represented by $R_{ii}COO\text{---}$. Here, $R_{ii}$ include those groups exemplified in $R_i$ mentioned above. The preferred examples of the acyloxy group include acetoxy group, propionyloxy group, benzoyloxy group, and the like.

In the present specification, the preferred examples of the aliphatic group include those groups exemplified in $R_i$ mentioned above.

In the present specification, the preferred examples of the aromatic group include, for instance, phenyl group, naphthyl group, biphenyl group, pyrrolyl group, pyridyl group, indolyl group, imidazolyl group, tolyl group, xylyl group, and the like.

In the present specification, the preferred examples of the aromatic-aliphatic group include, for instance, a phenylalkyl group of which alkyl group moiety has 1 to 15 carbon atoms, such as benzyl group and phenetyl group; styryl group; cinnamyl group; and the like.

Incidentally, a characteristic group such as hydroxyl group, thiol group, oxo group, thioxo group, amino group, nitro group, sulfate group, phosphate group, an alkoxy group, a halogen atom, an acyloxy group, or an acylthioxy group may be introduced into the above-mentioned aliphatic group, aromatic group or aromatic-aliphatic group, so long as the resulting compound has enhancing activity for NGF production.

Further, in the present specification, a sugar residue includes a group which can be represented by the structural formula in which one hydroxyl group is removed from a sugar. The sugar may be preferably a monosaccharide, as well as an oligosaccharide comprising 2 to 20 monosaccharide residues, or a sugar chain comprising 21 or more monosaccharide residues. In addition, the monosaccharide component constituting the sugar is not limited, and includes, for instance, D-glucose, D-fructose, L-rhamnose, galactose, mannose, as well as D-galactosamine, 2-deoxy-D-ribose, and the like. In the monosaccharide component constituting the sugar, there is no particular limitation in the steric structure such as D-form or L-form.

The compound used in the present invention can be represented by the above-mentioned general formula (1). Preferably, there can be exemplified compounds listed in Tables 1 and 2, xanthohumol represented by the formula (26) and safflomin A represented by the formula (27). The compound exemplified in the tables are those compounds in which X is the above-mentioned general formula (2) or (3) in the above-mentioned general formula (1). Here, $R_1$, $R_2$, $R_3$, $R_4$, $R_5$, and X in Tables 1 and 2 correspond to those of the above-mentioned general formula (1). The compound of the formula (N) is referred to as a compound (N). For instance, in Table 1, the compound of the formula (5) is referred to as a compound (5).

TABLE 1

| | Name | $R_1$ | $R_2$ | $R_3$ | $R_4$ | $R_5$ | X |
|---|---|---|---|---|---|---|---|
| Compound (5) | 3,4,2',4'-Tetraacetyl butein | H | OAc | OAc | H | H | |
| Compound (6) | 3,4-Dihydroxy-2',4'-dichloro chalcone | H | OH | OH | H | H | |
| Compound (7) | 3,4-Dihydroxy-2',4'-dimethoxy chalcone | H | OH | OH | H | H | |
| Compound (8) | 4-(3,4-Dihydroxyphenyl)-3-buten-2-one | H | OH | OH | H | H | |
| Compound (9) | 1-Adamantyl-3-(3,4-dihydroxyphenyl)-2-propen-1-one | H | OH | OH | H | H | |
| Compound (10) | Dihydrobutein | H | OH | OH | H | H | |
| Compound (11) | 1-Adamantyl-4-(3,4-dihydroxyphenyl)-3-buten-1-one | H | OH | OH | H | H | |
| Compound (12) | 1-Adamantyl-3-hydroxy-4-(3,4-dihydroxyphenyl)-butan-1-one | H | OH | OH | H | H | |

TABLE 1-continued

| | Name | R₁ | R₂ | R₃ | R₄ | R₅ | X |
|---|---|---|---|---|---|---|---|
| Compound(13) | Butein | H | OH | OH | H | H | |
| Compound(14) | Isoliquiritigenin | H | H | OH | H | H | |
| Compound(15) | Caffeic acid phenylethyl ester | H | OH | OH | H | H | |
| Compound(16) | Curcumin | H | OMe | OH | H | H | |

TABLE 2

| | Name | R₁ | R₂ | R₃ | R₄ | R₅ | X |
|---|---|---|---|---|---|---|---|
| Compound(17) | 3,4,5,2',4'-Pentahydroxy chalcone | H | OH | OH | OH | H | |
| Compound(18) | 3,4,2',5'-Tetrahydroxy chalcone | H | OH | OH | H | H | |
| Compound(19) | 3,4,3',4'-Tetrahydroxy chalcone | H | OH | OH | H | H | |
| Compound(20) | 3,4,3',5'-Tetrahydroxy chalcone | H | OH | OH | H | H | |

TABLE 2-continued
| Name | | $R_1$ | $R_2$ | $R_3$ | $R_4$ | $R_5$ | X |
|---|---|---|---|---|---|---|---|
| Compound(21) | 3,4,2'-Trihydroxy chalcone | H | OH | OH | H | H | 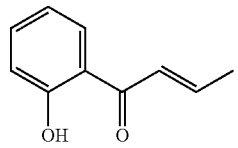 |
| Compound(22) | 3,4,2',3',4'-Pentahydroxy chalcone | H | OH | OH | H | H | 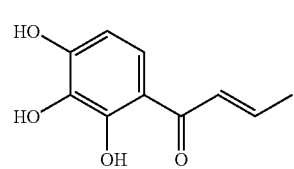 |
| Compound(23) | Rosmarinic acid | H | OH | OH | H | H | 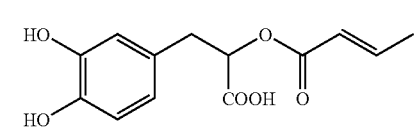 |
| Compound(24) | Xanthoangelol | H | H | OH | H | H | 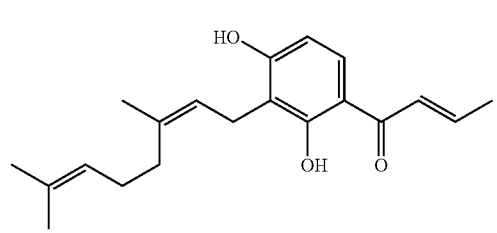 |
| Compound(25) | α-Hydroxybutein | H | OH | OH | H | H | 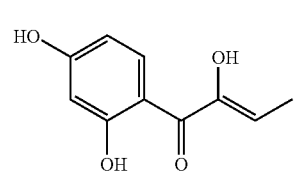 |
| Compound(26) | Xanthohumol | H | H | OH | H | H | 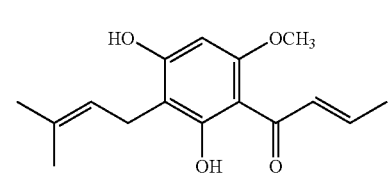 |
| Compound(27) | Safflomin A | H | H | OH | H | H | 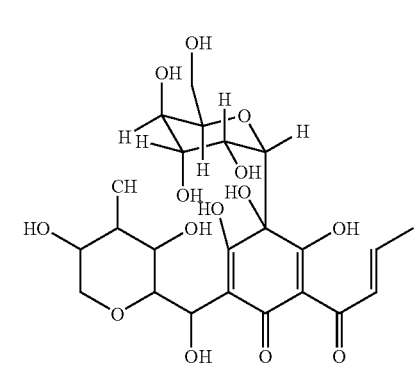 |

In addition, the preferred compound used as an effective ingredient in the present invention includes a compound having a flavonol bone structure in the structure, which is represented by the above-mentioned general formula (1) in which X is the above-mentioned general formula (4). Such a compound includes quercitrin represented by the above-mentioned general formula (1) in which each of $R_1$, $R_4$, $R_5$, and $R_7$ is hydrogen, each of $R_2$ and $R_3$ is hydroxyl group, and $R_6$ is α-L-rhamnose residue; quercetin in which each of $R_1$, $R_4$, $R_5$, $R_6$, and $R_7$ is hydrogen, and each of $R_2$ and $R_3$ is hydroxyl group (also referred to as 3,3'4'5,7-pentahydroxyflavone); myricetin in which each of $R_1$, $R_5$, $R_6$, and $R_7$ is hydrogen, and each of $R_2$, $R_3$, and $R_4$ is hydroxyl group (also referred to as 3,3'4'5,5',7-hexahydroxyflavone); and myricitrin in which each of $R_1$, $R_5$, and $R_7$ is hydrogen, each of $R_2$, $R_3$, and $R_4$ is hydroxyl group, and $R_6$ is α-L-rhamnose residue.

The compound used in the present invention is a commercially available compound. In addition, the compound can be properly prepared using as a starting raw material a chalcone, benzaldehyde, a benzaldehyde having hydroxyl group or hydroxyl groups as a substituent on benzene ring (for instance, 2,5-dihydroxybenzaldehyde), a chroman, cinnamic acid, cinnamic aldehyde, caffeic acid, or the like by a known method. Also, in a case where the compound exists as a natural product, the compound can be obtained by extraction from, for instance, a plant such as *Angelica keiskei, Carthamus tinctorius,* or hop according to a conventional method, and purifying the resulting extract.

In particular, among the compounds listed in the above-mentioned Tables 1 and 2, the compound (5), the compound (6), the compound (7), the compound (8), the compound (9), the compound (10), the compound (11), and the compound (12) are novel compounds newly prepared in the present invention. In other words, the present invention also provides these novel compounds, each having enhancing activity for NGF production. Each of these compounds can be prepared by a known method as mentioned above.

The processes for preparing the compounds (6), (7), (8) and (9) are not particularly limited. For instance, there can be used a known method disclosed in Japanese Patent Gazette No. 2913706. In other words, each compound can be obtained by condensing hydroxybenzaldehyde of which hydroxyl group is protected with tetrahydropyranyloxy group, with a compound having methyl ketone group by Claisen condensation reaction in the presence of a base such as barium hydroxide, and deprotecting tetrahydropyranyloxy group of the resulting condensate in the presence of an acid catalyst. During the Claisen condensation reaction, introduction of a protective group by tetrahydropyranyloxy group may not be carried out. In addition, as the catalyst for the Claisen condensation reaction, an acid such as hydrogen chloride can also be used besides a base.

The process for preparing the compound (12) is not particularly limited. There can be employed a process comprising subjecting to aldol-condensation of a methyl ketone compound with an aldehyde compound at a low temperature in the presence of lithium diisopropylamide. Further, the compound (11) can be prepared by introducing a proper leaving group to hydroxyl group at β-position of the compound (12), and thereafter removing the group with a base or the like. In addition, the compounds (6), (7), (8) and (9) can be prepared in the same manner as the process for preparing the compound (11) through the compound (12) described above.

The process for preparing the compound (5) is not particularly limited. The compound (5) can be prepared by acetylating a compound (13). For instance, a compound (13) and acetic anhydride are reacted in the presence of an alkali. Also, the donor for acetyl group may be a halogenated compound of acetic acid such as acetic chloride.

The process for preparing the compound (10) is not particularly limited. For instance, the compound (10) can be prepared by adding hydrogen gas to a solvent such as methanol containing the compound (13) in the presence of a catalyst such as palladium.

The salt of the compound represented by the above-mentioned general formula (1) includes, for instance, alkali metal salts, alkaline earth metal salts, and salts with an organic base. It is preferable that the base is a pharmacologically acceptable salt. The term "pharmacologically acceptable salt" as used herein refers to those which are substantially nontoxic against an organism, and are salts of a compound having enhancing activity for NGF production. The salts include, for instance, salts with sodium, potassium, calcium, magnesium, ammonium or protonated benzathine (N,N'-di-benzylethylenediamine), choline, ethanolamine, diethanolamine, ethylenediamine, meglamine (N-methylglucamine), benethamine (N-benzylphenetylamine), piperazine or tolomethamine (2-amino-2-hydroxymethyl-1,3-propanediol). These salts can be obtained, for instance, by converting a carboxylic acid represented by the above-mentioned general formula (1) in which X is the above-mentioned general formula (2) or (3), and n is 1, m is 0, Z or Z' is hydrogen atom, and Y or Y' is hydrogen atom to a salt by a known method. In addition, for instance, in the case of the compound represented by the above-mentioned general formula (1) in which X is the above-mentioned general formula (4), the salt of the compound can be obtained by converting phenolic hydroxyl group to a salt by a known method.

Further, the compound represented by the above-mentioned general formula (1) used in the present invention can be formed into a derivative (prodrug), for instance, which is easily hydrolyzed in the body, thereby exhibiting the desired effects. The preparation of the prodrug can be carried out according to a known method. The derivative may be a salt thereof.

The compound represented by the above-mentioned general formula (1) and a salt thereof used as an effective ingredient in the present invention, as mentioned above, each has enhancing activity for NGF production. The activity can be evaluated according to the method shown in Reference Example 1 set forth below. In addition, it is clear from Examples set forth below that the compound as the effective ingredient has the features of 1) showing a stronger enhancing activity at a low concentration; 2) having a wider concentration region showing enhancing activity; and/or 3) being lower in toxicity, than those of a known compound having enhancing activity for NGF production. According to the compound used as an effective ingredient in the present invention, owing to its enhancing activity for NGF production, as is clarified, for instance, in Example 18 set forth below, there can be exhibited an effect such that extension of axon is promoted through the enhancement of NGF production. In addittion, there are exhibited such effects that nerve cell death caused by active oxygen, nutritional famine, physical damage or the like is suppressed. Therefore, for instance, the compound would be useful for treatment or prevention of a disease that requires enhancement of NGF production as described below.

The compound represented by the above-mentioned general formula (1) used as an effective ingredient in the present invention is found from the results of screening according to the method shown as Reference Example 1 set forth below. Therefore, as one embodiment of the present invention, there is provided a method for screening a compound having enhancing activity for NGF production.

The compound and a salt thereof used as the effective ingredient in the present invention do not show toxicity even when a dose effective for enhancing activity of NGF production is administered to a living body. For instance, in the case of oral administration, there are no cases of death when either of butein [compound (13)], which is a compound having a chalcone backbone structure, or a pharmacologically acceptable salt thereof is administered to a mouse once at 1000 mg/kg. In addition, there are no cases of death when either of myricetin, which is a compound having a flavonol backbone structure, or a pharmacologically acceptable salt thereof is administered to a mouse once at 150 mg/kg.

The therapeutic agent or prophylactic agent for a disease that requires enhancement of NGF production, a first embodiment of the present invention, includes those which are prepared by combining the above-mentioned effective ingredient according to the present invention with a known pharmaceutical vehicle. In this embodiment of the present invention, as the salt which is the effective ingredient, the pharmacologically acceptable salts can be used.

The disease that requires enhancement of NGF production herein includes, for instance, dementia, nerve disorders, peripheral neuralgia, cerebral ischemia, diabetic neuropathy, and the like.

The therapeutic agent or prophylactic agent of the present invention is usually prepared by formulating the above-mentioned effective ingredient with a pharmacologically acceptable liquid or solid vehicle, and optionally adding thereto a solvent, a dispersant, an emulsifier, a buffer, a stabilizer, an excipient, a binder, a disintegrant, a lubricant, or the like, thereby being usually made into a solid agent such as a tablet, a granule, a powder, a fine powder, and a capsule, or a liquid agent such as a common liquid agent, a suspension agent or an emulsion agent. In addition, there can be also prepared a dry product which can be made liquid by adding an appropriate vehicle before use, and an external preparation.

The pharmaceutical vehicle can be selected depending upon the above-mentioned administration form and preparation form of the therapeutic agent or prophylactic agent. In the case of an orally administered preparation comprising a solid composition, a tablet, a pill, a capsule, a powder, a fine powder, a granule or the like can be formed by utilizing, for instance, starch, lactose, saccharose, mannitol, carboxymethyl cellulose, cornstarch, an inorganic salt or the like. In addition, during the preparation of the orally administered preparation, a binder, a disintegrant, a surfactant, a lubricant, a fluidity accelerator, a flavor, a colorant, a perfume, and the like can be further formulated. In the case of forming into a tablet or pill, for instance, the tablet or pill may be covered with a sugar-coating made of sucrose, gelatin or hydroxypropyl cellulose, or with a film made of a substance soluble in the stomach or intestine as occasion demands. In the case of an orally administered preparation comprising a liquid composition, the preparation can be prepared in the form of a pharmaceutically acceptable emulsion, solution, suspension, syrup, or the like, using purified water, ethanol, or the like, for instance, as a vehicle. Furthermore, an auxiliary agent such as a wetting agent or a suspending agent, a sweetener, a flavor, an antiseptic, or the like may be added as desired.

On the other hand, a non-orally administered preparation is prepared by dissolving or suspending the above-mentioned effective ingredient of the present invention in a diluent such as distilled water for injection, physiological saline, an aqueous solution of glucose, vegetable oil for injection, sesame oil, peanut oil, soybean oil, corn oil, propylene glycol or polyethylene glycol, by a conventional method, and adding a microbicide, a stabilizer, an osmotic regulator, a soothing agent, or the like as necessary. It is also possible to produce a solid composition which is dissolved in sterile water or a sterile solvent for injection before use.

The external preparation includes solid to semi-solid or semi-solid to liquid preparations for percutaneous administration or transmucosal (oral or intranasal) administration. The external preparation also includes suppositories and the like. For instance, the external preparation may be prepared as liquid preparations including emulsions, suspensions such as lotions, external tinctures, and liquids for transmucosal administration; ointments including oily ointments and hydrophilic ointments; medical adhesives for percutaneous administration or transmucosal administration such as films, tapes and poultices; and the like.

Each of the above-mentioned various preparations can be appropriately produced by conventional methods by utilizing known pharmaceutical vehicles and the like. The content of the effective ingredient in the preparation is not particularly limited, as long as the content is preferably the amount so that the effective ingredient can be administered within the dose described below in consideration of administration form, administration method and the like of the preparation.

The therapeutic agent or prophylactic agent of the present invention can be administered via an administration route appropriate for each of the preparation form. The administration method is not limited to specific one. The agent can be administered internally or externally (or topically) or by injection. The injection can be administered, for instance, intravenously, intramuscularly, subcutaneously, intracutaneously, or the like. As to an external preparation, a suppository may be administered according to its proper administration method.

In addition, the dose of the therapeutic agent or prophylactic agent is changeable and properly set depending upon its preparation form, administration method, purpose of use, age, body weight, symptom or the like of a mammal (for instance, a patient) to which the therapeutic agent or prophylactic agent is applied, or the like. Generally, in the case of human, the dose of the agent is an amount so that the dose for adult per day of the above-mentioned effective ingredient contained in the agent is preferably from 0.1 μg to 200 mg/kg. As a matter of course, the dose varies depending upon various conditions, so that an amount smaller than the dose mentioned above may be sufficient, or an amount exceeding the dose range may be required. Administration may be carried out once or in two or more divided portions in a day within the desired dose range.

NGF acts on nerve cell to allow extension of axon and sustenance of axon cell. Therefore, by enhancing the NGF production with the effective ingredient used in the present invention, the nervous system of a living body can be sustained and activated. Therefore, the therapeutic agent or prophylactic agent of the present invention is useful for treatment or prophylaxis of the above-mentioned various diseases.

The second embodiment of the present invention, the enhancer for NGF production comprising the above-mentioned effective ingredient according to the present invention may be the above-mentioned effective ingredient per se, or may be a composition comprising the above-mentioned effective ingredient. In this embodiment of the present invention, as the salt which is the effective ingredient, there is used a pharmacologically acceptable salt. The enhancer for NGF production can be produced by formulating the above-mentioned effective ingredient with other ingredients which can be used for the same application as the effective ingredient, and forming into a form of reagent usually used according to the above-mentioned process for producing the therapeutic agent or prophylactic agent. The content of the above-mentioned effective ingredient in the enhancer is not particularly limited, as long as the content may be preferably the amount so that the desired effects of the present invention can be obtained in consideration of administration form, administration method or the like of the enhancer. Also, the amount of the enhancer used is not particularly limited, as long as the desired effects of the present invention can be exhibited. Especially in the case where the enhancer is administered to a living body, the enhancer is preferably used in an amount so that the effective ingredient can be administered within the dose range of the effective ingredient in the above-mentioned therapeutic agent or prophylactic agent.

The enhancer for NGF production of the present invention can be used for activating nerve cell (for instance, improvement in learning and memorization ability). In addition, there can be conducted biochemical studies on nerve cell mechanisms and screening of drugs for dementia and nerve disorders by the method for enhancing NGF production described below using the enhancer.

The third embodiment of the present invention provides a method for enhancing NGF production, comprising administering the above-mentioned effective ingredient according to the present invention to an animal. In this embodiment, as the salt which is the effective ingredient, there is used a pharmacologically acceptable salt. This method can be carried out by administering the above-mentioned effective ingredient, preferably the enhancer for NGF production of the present invention, to an animal that is predicted to require or requires enhancement of NGF production. By administering the effective ingredient, the NGF production is enhanced. The administration method, dose, or the like of the effective ingredient may be preferably similar to that of the above-mentioned enhancer for NGF production. Here, the therapeutic agent or prophylactic agent, or the food, beverage or feed described below in the present invention can be used in the same manner as the enhancer for NGF production.

According to the method for enhancing NGF production, the biochemical studies regarding the nerve cell mechanisms can be carried out by activating nerve cell by the above method, and analyzing the tendency of the associated factors inside and outside the cell. In addition, according to the method for enhancing NGF production, there can be conducted screening of drugs for dementia, nerve disorders, and the like.

The fourth embodiment of the present invention provides a food, beverage or feed for enhancing NGF production. The food, beverage or feed comprises the above-mentioned effective ingredient according to the present invention. In this embodiment of the present invention, as the salt which is the effective ingredient, a pharmacologically acceptable salt or a salt of the same level of safety can be suitably used. Since the food, beverage or feed has enhancing action for NGF production, the food, beverage or feed is very useful in amelioration or prevention of symptoms for a disease that requires enhancement for NGF production described above, which is sensitive to the above effective ingredient.

The term "comprise or comprising" as referred to in the food, beverage or feed of the present invention includes the meanings of containing, adding and diluting. The term "containing" refers to an embodiment of containing the effective ingredient used in the present invention in the food, beverage or feed; the term "adding" refers to an embodiment of adding the effective ingredient used in the present invention to a raw material for the food, beverage or feed; and the term "diluting" refers to an embodiment of adding a raw material for the food, beverage or feed to the effective ingredient used in the present invention.

The method for preparing the food, beverage or feed of the present invention is not particularly limited. For instance, formulation, cooking, processing, and the like can be carried out in accordance with those generally employed for foods, beverages or feeds, and the food, beverage or feed can be prepared by the general methods for preparing a food, beverage or feed, as long as the resulting food, beverage or feed may contain the effective ingredient according to the present invention, wherein the effective ingredient has enhancing action for NGF production.

The food or beverage of the present invention is not particularly limited. The food or beverage includes, for instance, processed agricultural and forest products, processed stock raising products, processed marine products and the like, including processed grain products such as processed wheat products, processed starch products, processed premix products, noodles, macaronis, bread, bean jam, buckwheat noodles, wheat-gluten bread, rice noodle, fen-tiao, and packed rice cake; processed fat and oil products such as plastic fat and oil, tempura oil, salad oil, mayonnaise, and dressing; processed soybean products such as tofu products, soybean paste, and fermented soybeans; processed meat products such as ham, bacon, pressed ham, and sausage; marine products such as frozen ground fish, boiled fish paste, tubular roll of boiled fish paste, cake of ground fish, deep-fried patty of fish paste, fish ball, sinew, fish meat ham and sausage, dried bonito, products of processed fish egg, marine cans, and preserved food boiled down in soy sauce (tsukudani); milk products such as raw material milk, cream, yogurt, butter, cheese, condensed milk, powder milk, and ice cream; processed vegetable and fruit products such as paste, jam, pickled vegetables, fruit beverages, vegetable beverages, and mixed beverages; confectionaries such as chocolates, biscuits, sweet bun, cake, rice cake snacks, and rice snacks; alcohol beverages such as sake, Chinese liquor, wine, whisky, Japanese distilled liquor (shochu), vodka, brandy, gin, ram, beer, refreshing alcoholic beverages, fruit liquor, and liqueur; luxury drinks such as green tea, tea, oolong tea, coffee, refreshing beverages and lactic acid beverages; seasonings such as soy sauce, sauce, vinegar, and sweet rice wine; canned, binned or pouched foods such as rice topped cooked beef and vegetable, rice boiled together with meat and vegetables in a small pot, steamed rice with red beans, curry roux and rice, and other precooked foods; semi-dry or concentrated foods such as liver pastes and other spreads, soups for buckwheat noodles or wheat noodles, and concentrated soups; dry foods such as instant noodles, instant curry roux, instant coffee, powder juice, powder soup, instant soybean paste (miso) soup, precooked foods, precooked beverages, and precooked soup; frozen foods such as sukiyaki, pot-steamed hotchpotch, split and grilled eel, hamburger steak, shao-mai, dumpling stuffed with minced pork, various sticks, and fruit cocktails; solid foods; liquid foods (soups); spices; and the like, wherein the food or beverage comprises the above-mentioned effective ingredient according to the present invention.

The content of the above-mentioned effective ingredient in the food or beverage of the present invention is not particularly limited, and the content can be appropriately selected from the viewpoints of sensory ability and exhibition of activity. The content of the effective ingredient is, for instance, preferably 0.0001 parts by weight or more, more preferably from 0.001 to 10 parts by weight, per 100 parts by weight of the food, or for instance, preferably 0.0001 parts by weight or more, more preferably from 0.001 to 10 parts by weight, per 100 parts by weight of the beverage. Also, the food or beverage of the present invention may be taken such that the effective ingredient contained therein is taken in an amount of preferably from 0.01 to 100 mg/kg per day for adult.

In addition, according to the present invention, there is provided a feed for an organism comprising the above-mentioned effective ingredient according to the present invention having enhancing activity for NGF production. In another embodiment, the present invention also provides a method of feeding an organism, characterized by administering the above-mentioned effective ingredient to the organism. In still another embodiment, the present invention provides an organism feeding agent characterized in that the organism feeding agent comprises the above-mentioned effective ingredient.

In these inventions, the organism includes, for instance, culturing or breeding animals, pet animals, and the like. The culturing or breeding animal is exemplified by cattle, experimental animals, poultry, pisces, crustaceae or shellfish. The feed is exemplified by a feed for sustenance of and/or improvement in physical conditions. The organism feeding agent includes immersion agents, feed additives, and beverage additives.

According to these inventions, the same effects can be expected to be exhibited as those of the above-mentioned therapeutic agent or prophylactic agent of the present invention, on the basis of the enhancing activity for NGF production of the above-mentioned effective ingredient used in the present invention in the organism exemplified above for applying these. In other words, there can be expected exhibition of therapeutic or prophylactic effect for dementia or nerve disorders in the organism.

The above-mentioned effective ingredient used in the present invention is usually administered in an amount of preferably from 0.01 to 2000 mg per 1 kg of the subject organism per day. The administration can be made by adding and mixing the effective ingredient in a raw material for an artificially formulated feed, or mixing the effective ingredient with a powder raw material for an artificially formulated feed, and thereafter further adding and mixing the resulting mixture with other raw materials. In addition, the content of the above-mentioned effective ingredient in the feed is not particularly limited. The effective ingredient can be appropriately set in accordance with its purposes, and an appropriate proportion in the feed is from 0.001 to 15% by weight.

The artificially formulated feed includes feeds using animal-derived raw materials such as fish meal, casein, and squid meal; plant-derived raw materials such as soybean grounds, flour, and starch; microorganism raw materials such as yeasts for feed; animal fats and oils such as cod-liver oil and squid-liver oil; vegetable fats and oils such as soybean oil and rapeseed oil; and other raw materials such as vitamins, minerals, amino acids, and antioxidants; and the like as raw materials. In addition, feeds for fish such as fish minced meat are also included.

The method for preparing the feed of the present invention is not particularly limited. In addition, the formulation may be in accordance with those of general feeds, as long as the effective ingredient according to the present invention having enhancing activity for NGF production is contained in the feed produced.

Also, the above-mentioned effective ingredient having enhancing activity for NGF production can be administered by directly adding the above-mentioned effective ingredient to water, seawater, or the like in a pool, a water tank, a water reservoir, or a feeding range, and immersing a subject organism into the resulting solution. The immersion method is especially effective when the amount of intake of the feed of the subject organism is lowered. The concentration of the effective ingredient according to the present invention having enhancing action for NGF production in water or seawater is not particularly limited, and the effective ingredient may be used in accordance with its purposes. It is appropriate that the concentration is preferably from 0.00001 to 1% by weight.

Also, a beverage comprising the above-mentioned effective ingredient according the present invention, having enhancing activity for NGF production may be given to a subject organism as a feeding drink. The concentration of the effective ingredient used in the present invention having enhancing action for NGF production in the beverage is not particularly limited, and the effective ingredient may be used in accordance with its purposes. It is appropriate that the concentration is preferably from 0.0001 to 1% by weight.

The organism feeding agent, for instance, an immersion agent, a feed additive, or a beverage additive comprising the above-mentioned effective ingredient according to the present invention having enhancing action for NGF production may be prepared by known formulation and preparation method. The content of the effective ingredient in the organism feeding agent is not particularly limited, so long as the desired effects of the present invention can be obtained.

The organism to which the present invention can be applied is not limited. The culturing or breeding animals include cattle such as Equus, Bos, Porcus, Ovis, Capra, Camelus, and Lama; experimental animals such as mice, rats, guinea pigs, and rabbits; poultry such as Chrysolophus, ducks, Meleagris, and Struthioniformes; pisces such as Pagrus, Oplegnathidae, Paralichthys, plaice, Seriola, young Seriola, amberjack, Thunna, *Caranx delicatissimus,* Plecoglossus, Salmo, Oncorhynchus, Fugu, Anguilla, Misguirus, and Parasilurus; Crustaceae such as Penaidae, black tiger shrimp, *Penaeus roentalis,* and *Portulis trituberculatus;* and shellfish such as abalones (awabi), turban shells, scallops, and oysters; and the pet animals includes dogs, cats, and the like, so that the feed can be widely applied to animals on land and in water.

By allowing a subject organism to take the feed comprising the above-mentioned effective ingredient used in the present invention having enhancing action for NGF production, or immersing a subject organism into a solution containing the above-mentioned effective ingredient used in the present invention having enhancing action for NGF production, the physical conditions of the cattle, experimental animals, poultry, pisces, Caustacea, shellfish, pet animals or the like can be well sustained and ameliorated.

The food, beverage or feed of the present invention does not have any particular limitation on its shape, as long as the food, beverage or feed comprises the above-mentioned effective ingredient according to the present invention in an amount necessary for exhibiting its enhancing activity for NGF production. For instance, such shapes include orally taken shapes such as tablets, granules and capsules.

Further, in the fifth embodiment, the present invention provides use of the above-mentioned effective ingredient according to the present invention in the preparation of a therapeutic agent or prophylactic agent for a disease that requires enhancement of NGF production, an enhancer for NGF production, or a food, beverage or feed for enhancing NGF production. The use embodiments include use embodiments of the above-mentioned effective ingredient in the preparation of the therapeutic agent or prophylactic agent, the enhancer for NGF production, or the food, beverage or feed for enhancing NGF production of the present invention mentioned above. For instance, as the use of the above-mentioned effective ingredient in the preparation of a therapeutic agent or prophylactic agent for a disease that requires enhancement of NGF production, or an enhancer for NGF production, there are exemplified the use in the preparation of a solid agent such as a tablet, a granule, a powder, a fine powder, and a capsule, a liquid agent such as a common liquid agent, a suspension agent, or an emulsion agent, or a dry product which can be liquefied by adding an appropriate vehicle before use.

As clarified in Examples set forth below, the effective ingredient according to the present invention has the features of 1) showing a stronger enhancing activity at a low concentration; 2) having a wider concentration region showing enhancing activity; and/or 3) being lower in toxicity, as compared to those known compounds having enhancing activity for NGF production. Therefore, the therapeutic agent or prophylactic agent, or the food, beverage or feed of the present invention, each comprising the above effective ingredient, is useful for treatment or prevention of a disease that requires enhancement for NGF production. In addition, the enhancer for NGF production comprising the above-mentioned effective ingredient is useful for biochemical studies on nerve cell mechanisms and screening of drugs for dementia, nerve disorders or the like.

EXAMPLES

The present invention will be more concretely described below by means of Preparation Examples, Examples, and the like, without intending to limit the present invention thereto. Here, "%" in Preparation Examples, Examples and the like means "% by weight" unless otherwise specified.

Preparation Example 1

Preparation of Butein [Compound (13)]

One gram (6.6 mmol) of 2',4'-dihydroxy acetophenone (manufactured by Tokyo Kasei Kogyo), 912 mg (6.6 mmol) of 3,4-dihydroxy benzaldehyde (manufactured by Tokyo Kasei Kogyo), and 80 mg (0.32 mmol) of pyridinium p-toluenesulfonate (manufactured by Tokyo Kasei Kogyo) were dissolved in 26 mL of dichloromethane, and the resulting mixture was stirred at room temperature for 30 minutes. Thereafter, 10 mL of 3,4-dihydro-2H-pyran (manufactured by Tokyo Kasei Kogyo) was added thereto, and the resulting mixture was stirred at room temperature for additional 3 hours. The reaction solution was washed twice with water, and concentrated under reduced pressure. Subsequently, the resulting oily product was dissolved in 26 mL of methanol, and 2.15 g of barium hydroxide octahydrate was added thereto. The resulting mixture was stirred at 40° C. for about 20 hours. The reaction solution was diluted with 26 mL of methanol, and thereafter the pH of the resulting solution was adjusted to near neutrality with 1 N hydrochloric acid. The reaction solution was extracted with ethyl acetate, and the resulting organic layer was sequentially washed with saturated aqueous sodium bicarbonate, 10% aqueous citric acid and saturated aqueous sodium chloride. Thereafter, the resulting organic layer was dried over anhydrous magnesium sulfate, and concentrated under reduced pressure. The concentrate was subjected to chromatography using a silica gel column (manufactured by Fuji Silycia Kagaku K.K.), which is hereinafter referred to as silica chromatography, with a developing solvent of hexane:ethyl acetate (volume ratio)=5:1, thereby giving the tetrahydroxypyran (THP) form of a compound (13). The THP form of the compound (13) was dissolved in 26 mL of methanol, and 67 mg (0.264 mmol) of sulfosalicylic acid dehydrate was added thereto. The resulting mixture was stirred at room temperature for 3 hours. The reaction solution was diluted with ethyl acetate, and thereafter washed with saturated aqueous sodium chloride. The resulting solution was dried over anhydrous magnesium sulfate, and concentrated under reduced pressure. One gram of the compound (13) was recrystallized from the concentrate with hexane and ethyl acetate (yield: 56%). The nuclear magnetic resonance (NMR) spectrum and the mass spectrum of the compound (13) were analyzed with JNM-A500 (manufacture by JEOL LTD.) and MS (DX302) mass spectrometer (manufacture by JEOL LTD.), respectively, to determine its structure. The determination results of the NMR spectrum and the mass spectrum are shown below.

$^1$H NMR: δ 6.26 (1H, d, $J_{3',5'}$ 2 Hz, H-3'), 6.38 (1H, dd, $J_{5',6'}$ 9 Hz, H-5'), 6.80 (1H, d, $J_{5,6}$ 8 Hz, H-5), 7.19 (1H, dd, $J_{2,6}$ 2 Hz, H-6), 7.26 (1H, d, H-2), 7.64 (2H, m, H-α,β), 8.12 (1H, d, H-6')

Here, the sample was dissolved in deuterium dimethyl sulfoxide, and the value of the chemical shift of the residual dimethyl sulfoxide was expressed as 2.49 ppm.

FAB-MS: m/z 273 (M+H)$^+$ (Here, glycerol was used as the matrix.)

Preparation Example 2

Preparation of 3,4,5,2',4'-Pentahydroxy chalcone [Compound (17)]

The same procedures as in Preparation Example 1 were carried out using 0.5 g (2.9 mmol) of 2',4'-dihydroxy acetophenone and 0.4 g (2.9 mmol) of 3,4-dihydroxy benzaldehyde as starting materials, to give 600 mg of a compound (17) (yield: 72%). The determination results of the NMR spectrum and the mass spectrum are shown below.

$^1$H-NMR: 6.23 (1H, d, $J_{3',5'}$ 2 Hz, H-3'), 6.36 (1H, dd, $J_{5',6'}$ 9 Hz, H-5'), 6.78 (2H, s, H-2, 6), 7.54 (2H, m, H-α,β), 8.07 (1H, d, H-6')

Here, the sample was dissolved in deuterium dimethyl sulfoxide, and the value of the chemical shift of the residual dimethyl sulfoxide was expressed as 2.49 ppm.

FAB-MS: m/z 289 (M+H)$^+$ (Here, glycerol was used as the matrix.)

Preparation Example 3

Preparation of 3,4,2',5'-Tetrahydroxy chalcone [Compound (18)]

The same procedures as in Preparation Example 1 were carried out using 497 mg (3.3 mmol) of 2',5'-dihydroxy acetophenone (manufactured by Tokyo Kasei Kogyo) and 451 mg (3.3 mmol) of 3,4-dihydroxy benzaldehyde as starting materials, to give 760 mg of a compound (18) (yield: 85%). The determination results of the NMR spectrum and the mass spectrum are shown below.

$^1$H-NMR: δ 6.79 (1H, d, $J_{5,6}$ 8 Hz, H-5), 6.81 (1H, d, $J_{3',4'}$ 9 Hz, H-3'), 6.00 (1H, dd, $J_{4',6'}$ 3 Hz, H-4'), 7.17 (1H, dd, $J_{2,6}$ 2 Hz, H-6), 7.23 (1H, d, H-2), 7.44 (1H, d, H-6'), 7.55 (1H, d, $J_{\alpha,\beta}$ 15 Hz, H-α), 7.66 (1H, d, H-β)

Here, the sample was dissolved in deuterium dimethyl sulfoxide, and the value of the chemical shift of the residual dimethyl sulfoxide was expressed as 2.49 ppm.

FAB-MS: m/z 273 (M+H)$^+$ (Here, glycerol was used as the matrix.)

Preparation Example 4

Preparation of 3,4,3',4'-Tetrahydroxy chalcone [Compound (19)]

The same procedures as in Preparation Example 1 were carried out using 515 mg (3.4 mmol) of 3',4'-dihydroxy acetophenone (manufactured by Tokyo Kasei Kogyo) and 468 mg (3.4 mmol) of 3,4-dihydroxy benzaldehyde as starting materials, to give 272 mg of a compound (19) (yield:30%). The determination results of the NMR spectrum and the mass spectrum are shown below.

$^1$H-NMR: δ 6.78 (1H, d, $J_{5,6}$ 8 Hz, H-5), 6.83 (1H, dd, $J_{5',6'}$ 8 Hz, H-5'), 7.11 (1H, dd, $J_{2,6}$ 2 Hz, H-6), 7.18 (1H, d, H-2), 7.46 (1H, d, $J_{2',6'}$ 2 Hz, H-2'), 7.48 (2H, m, H-α,β), 7.54 (1H, dd, H-6')

Here, the sample was dissolved in deuterium dimethyl sulfoxide, and the value of the chemical shift of the residual dimethyl sulfoxide was expressed as 2.49 ppm.

FAB-MS: m/z 273 (M+H)$^+$ (Here, glycerol was used as the matrix.)

Preparation Example 5

Preparation of 3,4,3',5'-Tetrahydroxy chalcone [Compound (20)]

The same procedures as in Preparation Example 1 were carried out using 816 mg (5.4 mmol) of 3,5'-dihydroxy acetophenone (manufactured by Tokyo Kasei Kogyo) and 741 mg (5.4 mmol) of 3,4-dihydroxy benzaldehyde as starting materials, to give 605 mg of a compound (20) (yield: 41%). The determination results of the NMR spectrum and the mass spectrum are shown below.

$^1$H-NMR: δ 6.45 (1H, dd, $J_{2',4'}$ 2, $J_{4',6'}$ 2 Hz, H-4'), 6.77 (1H, d, $J_{5,6}$ 8 Hz, H-5), 6.87 (2H, d, H-2',6'), 7.11 (1H, dd, $J_{2,6}$ 2 Hz, H-6), 7.18 (1H, d, H-2), 7.35 (1H, d, $J_{\alpha,\beta}$ 16 Hz, H-α), 7.51 (1H, d, H-β)

Here, the sample was dissolved in deuterium dimethyl sulfoxide, and the value of the chemical shift of the residual dimethyl sulfoxide was expressed as 2.49 ppm.

FAB-MS: m/z 272 (M+H)$^+$ (Here, glycerol was used as the matrix.)

Preparation Example 6

Preparation of 3,4,2'-Trihydroxy chalcone [Compound (21)]

The same procedures as in Preparation Example 1 were carried out using 890 g (6.5 mmol) of 2'-hydroxy acetophenone (manufactured by Tokyo Kasei Kogyo) and 902 mg (6.5 mmol) of 3,4-dihydroxy benzaldehyde as starting materials, to give 715 mg of a compound (21) (yield: 43%). The determination results of the NMR spectrum and the mass spectrum are shown below.

$^1$H-NMR: δ 6.81 (1H, d, $J_{5,6}$ 8 Hz, H-5), 6.98 (2H, m, H-3',5'), 7.22 (1H, dd, $J_{2,6}$ 8 Hz, H-6), 7.29 (1H, d, H-2), 7.53 (1H, $J_{3',4'}$ 8, $J_{4',5'}$ 8, $J_{4',6'}$ 2 Hz, td, H-4'), 7.71 (2H, m, H-α,β), 8.21 (1H, dd, $J_{5',6'}$ 8 Hz, H-β)

Here, the sample was dissolved in deuterium dimethyl sulfoxide, and the value of the chemical shift of dimethyl sulfoxide was expressed as 2.49 ppm.

FAB-MS: m/z 257 (M+H)$^+$ (Here, glycerol was used as the matrix.)

Preparation Example 7

Preparation of 3,4,2',3',4'-Pentahydroxy chalcone [Compound (22)]

The same procedures as in Preparation Example 1 were carried out using 605 mg (3.6 mmol) of 2',3',4'-trihydroxy acetophenone (manufactured by Tokyo Kasei Kogyo) and 500 mg (3.6 mmol) of 3,4-dihydroxy benzaldehyde as starting materials, to give 622 mg of a compound (22) (yield: 60%). The determination results of the NMR spectrum and the mass spectrum are shown below.

$^1$H-NMR: δ 6.41 (1H, d, $J_{5',6'}$ 9 Hz, H-5'), 6.80 (1H, d, $J_{5,6}$ 8 Hz, H-5), 7.19 (1H, dd, $J_{2,6}$ 2 Hz, H-6), 7.26 (1H, d, H-2), 7.64 (2H, m, H-α,β), 7.68 (1H, d, H-6')

Here, the sample was dissolved in deuterium dimethyl sulfoxide, and the value of the chemical shift of the residual dimethyl sulfoxide was expressed as 2.49 ppm.

FAB-MS: m/z 289 (M+H)$^+$ (Here, glycerol was used as the matrix.)

Preparation Example 8

Preparation of Xanthoangelol [Compound (24)]

Four-hundred and eighty grams of a dried product of *Angelica keiskei* (manufactured by Sakamoto Kanpodo) was pulverized with a food processor, and extracted twice with about 1 L of ethyl acetate. The resulting organic layer fraction was concentrated under reduced pressure, and thereafter the concentrate was subjected to silica chromatography. Then, the adsorbed substance was eluted stepwise by sequentially using a chloroform/methanol mixture in a ratio of 100:1 (600 mL) and 12:1 (600 mL). An 8 mL portion was collected per fraction. the obtained fractions of on and after Fraction No. 76 were combined, and concentrated under reduced pressure. The concentrate was subjected to silica chromatography using a developing solvent of hexane:ethyl acetate=1.8:1, thereby giving fractions in which a compound (24) was contained in a high concentration, Fraction Nos. 25 to 50. About 200 mg of the high purity compound (24) was obtained from these fractions by recrystallization with hexane and ethyl acetate. The determination results of the NMR spectrum are shown below.

$^1$H-NMR: δ 1.58 (3H, s, -Me), 1.66 (3H, s, -Me), 1.81 (3H, s, -Me), 2.08 (4H, m), 3.48 (2H, d, J 7 Hz), 5.04 (1H, m), 5.29 (1H, m), 6.40 (1H, d $J_{5',6'}$ 9 Hz, H-5'), 6.86 (2H, d, $J_{5,6}$ 9, $J_{2,3}$ 9 Hz, H-2,6), 7.45 (1H, d, $J_{α,β}$ 15 Hz, H-α), 7.54 (2H, d, H-3,5), 7.71 (1H, d, H-6'), 7.82 (1H, d, H-β)

Here, the sample was dissolved in deuterium chloroform, and the value of the chemical shift of the residual chloroform was expressed as 7.24 ppm.

Preparation Example 9

Preparation of α-Hydroxybutein [Compound (25)]

Two-hundred milligrams (0.455 mmol) of a compound (5) prepared in Example 1 described below was dissolved in 455 mL of 10 mM sodium carbonate buffer to carry out the reaction at room temperature for 5 hours. The reaction solution was concentrated, and subjected to chromatography using a reversed-phase column (hereinafter referred to as reversed-phase chromatography). The column used was TSK gel ODS-80 Ts (diameter: 21.5 mm, length: 30 cm, manufactured by Tosoh Corporation). The elution ratio of Solvent A (0.1% aqueous trifluoroacetic acid) and Solvent B (mixture of distilled water and acetonitrile in a volume ratio of 1:1, containing 0.1% trifluoroacetic acid) was such that the ratio of Solvent B was increased linearly from 0 to 100% from 0 to 120 minutes, and the ratio of Solvent B was retained at 100% for the next 20 minutes. The elution rate was 5 ml/minute, and the detection was carried out at 215 nm.

The fractions including a peak having a retention time of 66.0 minutes were collected, and concentrated to dryness, to give 5.0 mg of a compound (25) (yield: 2.5%). The determination results of the NMR spectrum and the mass spectrum are shown below.

$^1$H-NMR: δ 6.59 (1H, s, -H-β), 6.72 (1H, dd, $J_{3',5'}$ 1.5, $J_{5',6'}$ 8.5 Hz, H-5'), 6.85 (1H, d, H-3'), 6.87 (1H, d, $J_{5,6}$ 8.5 Hz, H-5), 7.20 (1H, dd, $J_{2,6}$ 2.0 Hz, H-6), 7.46 (1H, d, H-2), 7.54 (1H, d, H-6')

Here, the sample was dissolved in deuterium dimethyl sulfoxide, and the value of the chemical shift of the residual dimethyl sulfoxide was expressed as 2.49 ppm.

FAB-MS: m/z 271 (M—H$_2$O+H)$^+$ (Here, glycerol was used as the matrix.)

Preparation Example 10

Preparation of Xanthohumol

For the purpose of purifying xanthohumol, 1.9 mg of a fraction of xanthohumol derived from hop (manufactured by Hopsteiner) was subjected to reversed-phase chromatography. The column used was TSK gel ODS-80 TsQA (diameter: 4.6 mm, length: 25 cm, manufactured by Tosoh Corporation). The elution ratio of Solvent A (mixture of distilled water and acetonitrile in a volume ratio of 3:1, containing 0.1% trifluoroacetic acid) and Solvent B (mixture of distilled water and acetonitrile in a volume ratio of 1:3, containing 0.1% trifluoroacetic acid) was such that the ratio of Solvent B was increased linearly from 50 to 100% from 0 to 20 minutes, the ratio of Solvent B was retained at 100% for the next 5 minutes, and the ratio of Solvent B was finally decreased to 50% and retained thereat for 5 minutes. The elution rate was 1 ml/minute, and the detection was carried out at 215 nm. The fractions including a peak having a retention time of 12.8 minutes were collected, and concentrated to dryness, to give about 0.3 mg of a compound. The resulting compound was analyzed by NMR. As a result, the compound was confirmed to be xanthohumol represented by the formula (26).

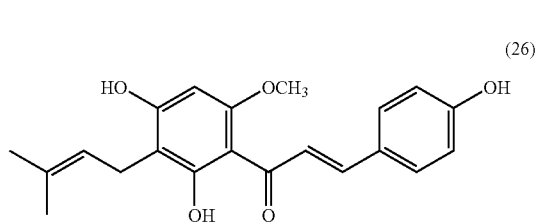

(26)

The determination results of the NMR spectrum and the mass spectrum are shown below.

$^1$H-NMR: δ 1.60 (3H, s, -Me), 1.69 (3H, s, -Me), 3.12 (2H, d, 7 Hz, H-1"$_{a, b}$), 3.86 (3H, s, -OMe), 5.13 (1H, s, H-2"), 6.07 (1H, s, H-5'), 6.83 (2H, d, $J_{2,3}$ 9 Hz, $J_{5,6}$ 9 Hz, H-2,6), 7.56 (2H, d, H-3,5), 7.66 (1H, d, $J_{\alpha,\beta}$ 16 Hz), 7.75 (1H, d), 10.05 (1H, s, OH-4), 10.55 (1H, s, OH-4'), 14.63 (1H, s, OH-2')

Figure 9:
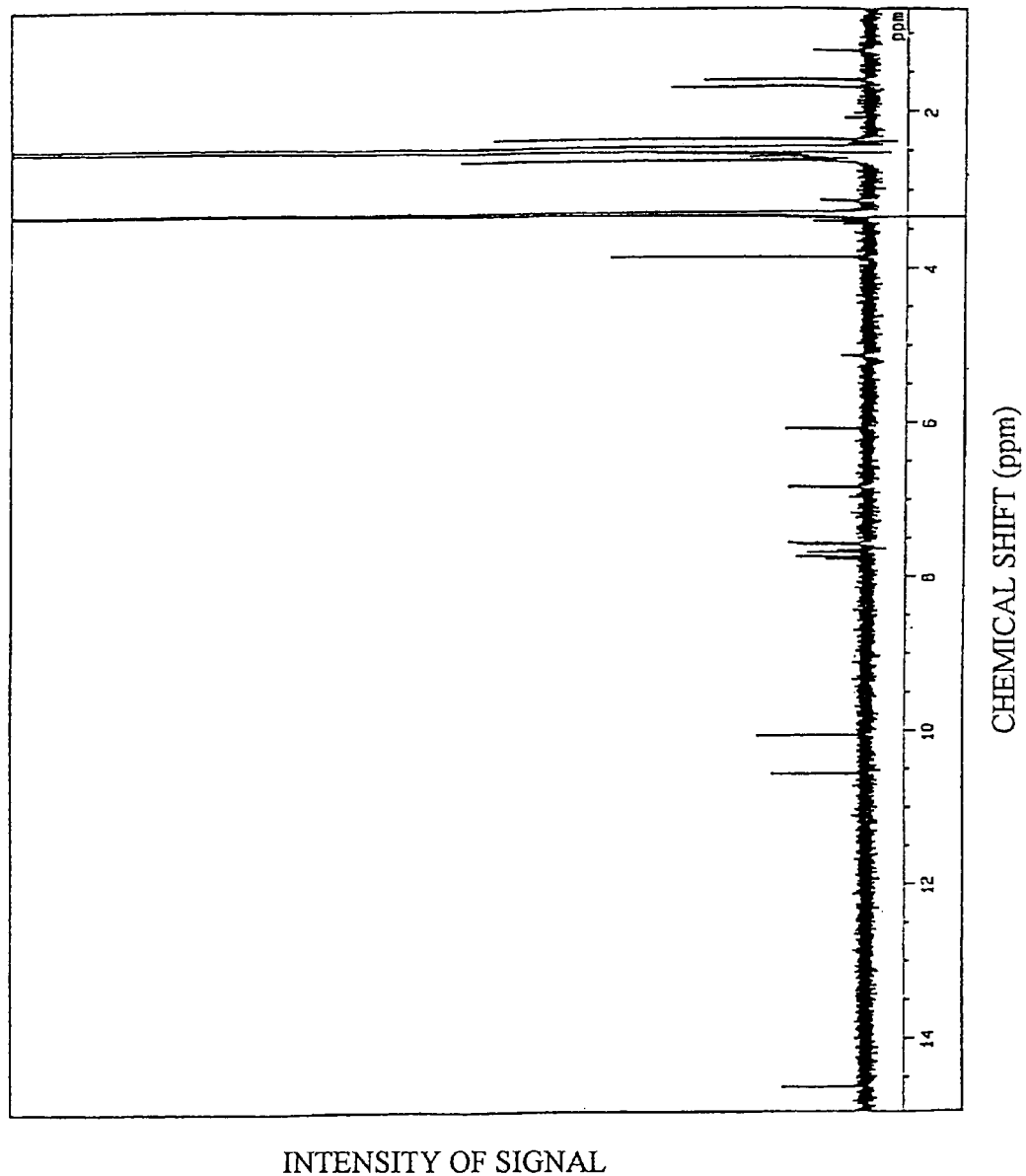
FIG. 9 is a graph showing $^1$H-NMR spectrum of a compound (27).

Here, the sample was dissolved in deuterium dimethyl sulfoxide, and the value of the chemical shift of the residual dimethyl sulfoxide was expressed as 2.49 ppm. FIG. 9 shows the $^1$H-NMR spectrum of xanthohumol obtained. In FIG. 9, the axis of abscissas is the value of chemical shift (ppm), and the axis of ordinates is the intensity of signal.

FAB-MS: m/z 355 (M+H)$^+$ (Here, glycerol was used as the matrix.)

Example 1

Preparation of 3,4,2',4'-Tetraacetyl butein [Compound (5)]

One gram (3.7 mmol) of the compound (13) prepared in Preparation Example 1 was dissolved in 50 mL of dichloromethane. Acetic anhydride (18.5 mmol), triethylamine (18.5 mmol) and dimethylaminopyridine (1.8 mmol) were added thereto under ice cooling, and the resulting mixture was stirred at room temperature for 1 hour. The reaction solution was sequentially washed with saturated aqueous sodium bicarbonate, 10% aqueous citric acid, and saturated aqueous sodium chloride. Thereafter, the resulting solution was dried over anhydrous magnesium sulfate, and concentrated under reduced pressure. A compound (5) (1.5 g, yield: 90%) was recrystallized from the concentrate with hexane and chloroform. The determination results of the NMR spectrum and the mass spectrum are shown below.

$^1$H-NMR: δ 2.23 (3H, s, -OAc), 2.29 (3H, s, -OAc), 2.30 (3H, s, -OAc), 2.31 (3H, s, -OAc), 7.00 (1H, d, $J_{3',6'}$ 2, H-3'), 7.09 (1H, d, $J_{\alpha,\beta}$ 16 Hz, H-α), 7.12 (1H, dd, $J_{5',6'}$ 8 Hz, H-5'), 7.23 (1H, d, $J_{5,6}$ 8 Hz, H-5), 7.41 (1H, d, $J_{2,6}$ 2 Hz, H-2), 7.44 (1H, dd, H-6), 7.52 (1H, d, H-β), 7.71 (1H, d, H-6')

Here, the sample was dissolved in deuterium chloroform, and the value of the chemical shift of the residual chloroform was expressed as 7.24 ppm. FIG. 1 shows the $^1$H-NMR spectrum of the compound (5). In FIG. 1, the axis of abscissas is the value of chemical shift (ppm), and the axis of ordinates is the intensity of signal.

FAB-MS: m/z 441 (M+H)$^+$ (Here, glycerol was used as the matrix.)

Example 2

Preparation of 3,4-Dihydroxy-2',4'-dichlorochalcone [Compound (6)]

The same procedures as in Preparation Example 1 were carried out using 680 mg (3.6 mmol) of 2',4'-dichloroacetophenone (manufactured by Sigma) and 500 mg (3.6 mmol) of 3,4-dihydroxy benzaldehyde as starting materials, to give 320 mg of a compound (6) (yield: 29%). The determination results of the NMR spectrum and the mass spectrum are shown below.

$^1$H-NMR: δ 6.76 (1H, d, $J_{5,6}$ 8 Hz, H-5), 6.88 (1H, d, $J_{\alpha,\beta}$ 16 Hz, H-α), 7.04 (1H, dd, $J_{2,6}$ 2 Hz, H-6), 7.11 (1H, d, H-2), 7.23 (1H, d, H-β), 7.55 (2H, m, H-5',6'), 7.74 (1H, s, H-3')

Figure 2:
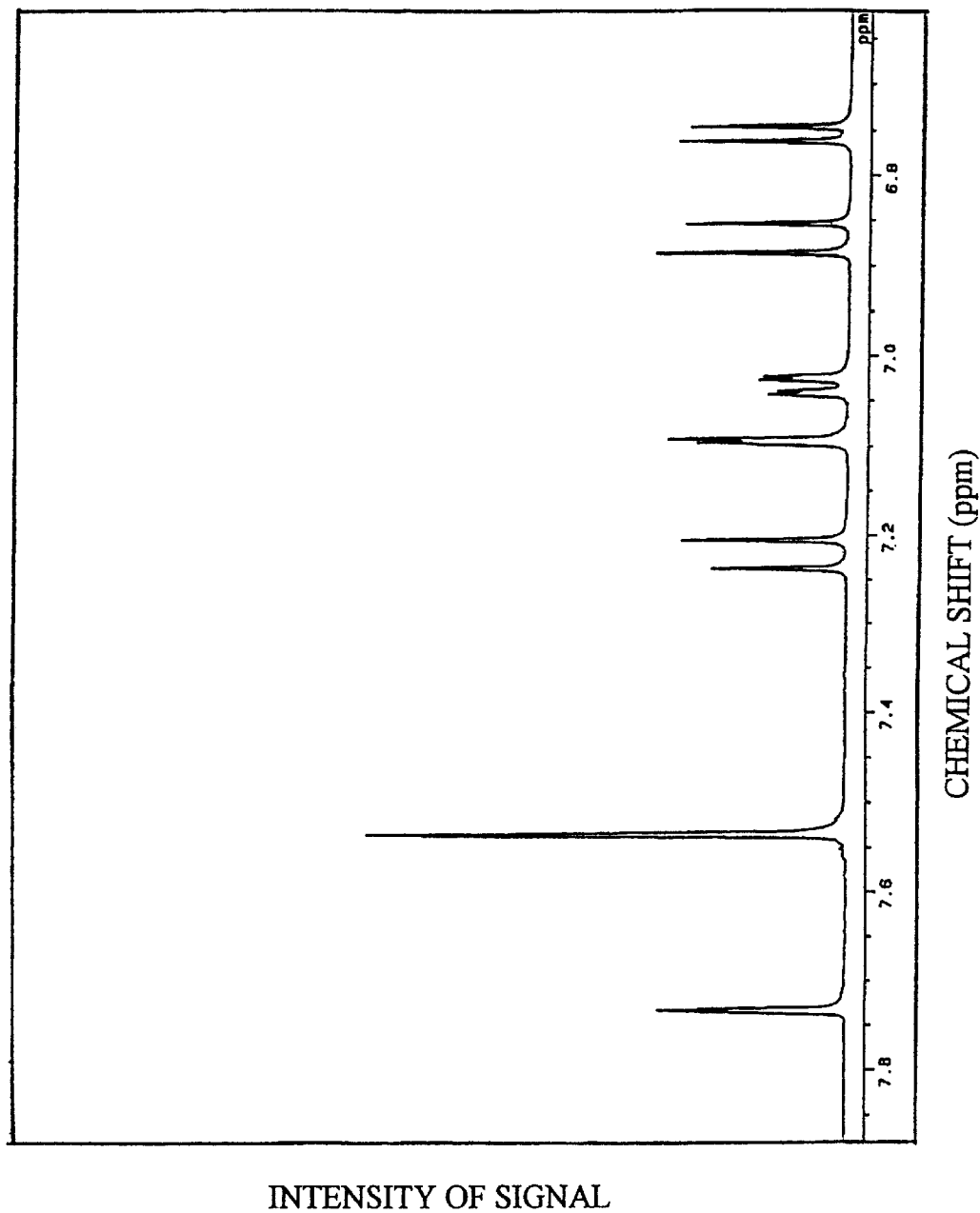
FIG. 2 is a graph showing $^1$H-NMR spectrum of a compound (6).

Here, the sample was dissolved in deuterium dimethyl sulfoxide, and the value of the chemical shift of the residual dimethyl sulfoxide was expressed as 2.49 ppm. FIG. 2 shows the $^1$H-NMR spectrum of the compound (6). In FIG. 2, the axis of abscissas is the value of chemical shift (ppm), and the axis of ordinates is the intensity of signal.

FAB-MS: m/z 309 (M+H)$^+$ (Here, glycerol was used as the matrix.)

Example 3

Preparation of 3,4-Dihydroxy-2',4'-dimethoxy chalcone [Compound (7)]

The same procedures as in Preparation Example 1 were carried out using 648 mg (3.6 mmol) of 2',4'-dimethoxy acetophenone (manufactured by Tokyo Kasei Kogyo) and 500 mg (3.6 mmol) of 3,4-dihydroxy benzaldehyde as starting materials, to give 600 mg of a compound (7) (yield: 56%). The determination results of the NMR spectrum and the mass spectrum are shown below.

$^1$H-NMR: δ 4.10 (3H, s, -OMe), 4.40 (3H, s, -OMe), 6.62 (1H, dd, $J_{3',6'}$ 2, $J_{5',6'}$ 9 Hz, H-5'), 6.67 (1H, d, H-3'), 6.77 (1H, d, $J_{5,6}$ 8 Hz, H-5), 6.99 (1H, dd, $J_{2,6}$ 2 Hz, H-6), 7.08 (1H, d, H-2), 7.25 (1H, d, $J_{\alpha,\beta}$ 16 Hz, H-α), 7.39 (1H, d, H-β), 7.67 (1H, d, H-6')

Figure 3:
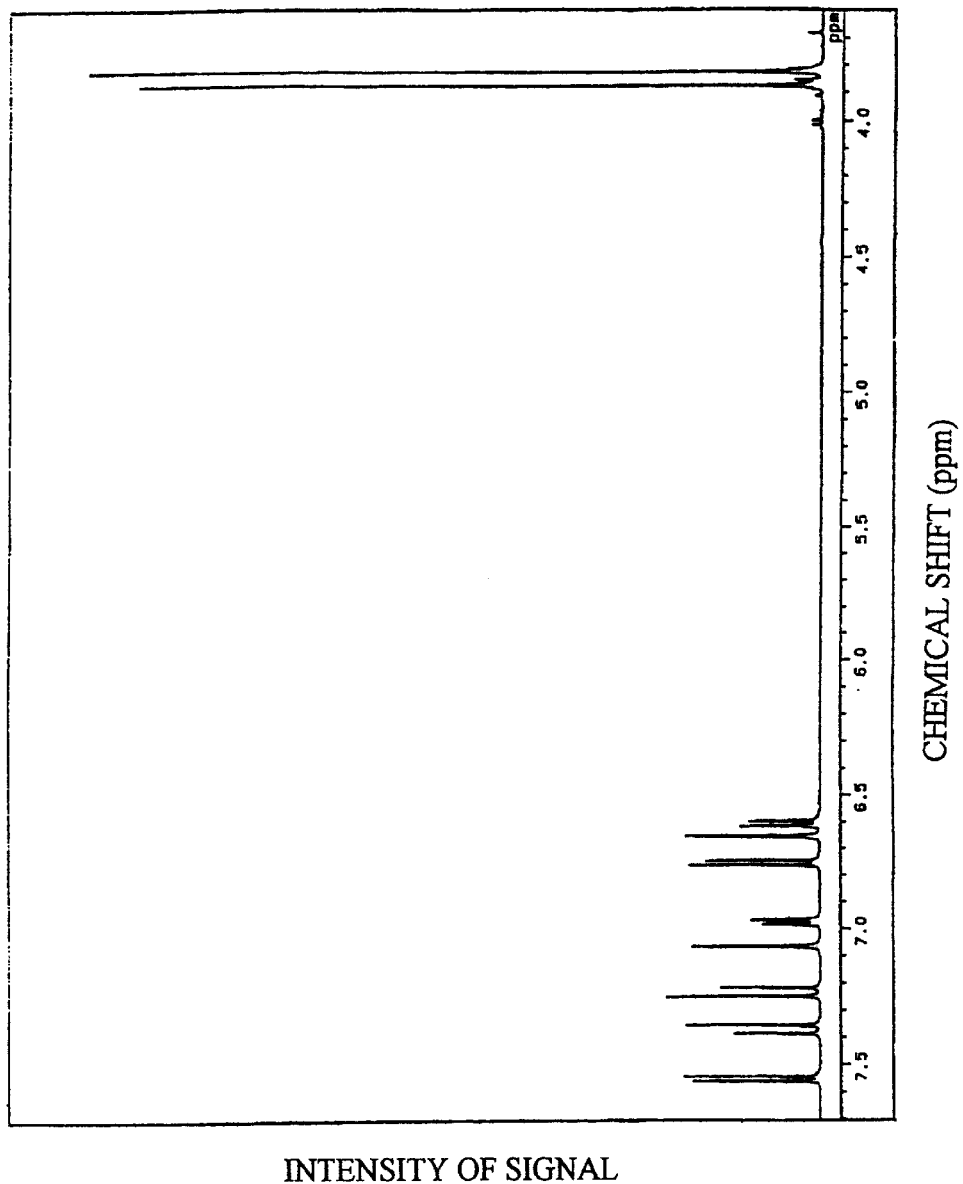
FIG. 3 is a graph showing $^1$H-NMR spectrum of a compound (7).

Here, the sample was dissolved in deuterium dimethyl sulfoxide, and the value of the chemical shift of the residual dimethyl sulfoxide was expressed as 2.49 ppm. FIG. 3 shows the $^1$H-NMR spectrum of the compound (7). In FIG. 3, the axis of abscissas is the value of chemical shift (ppm), and the axis of ordinates is the intensity of signal.

FAB-MS: m/z 301 (M+H)$^+$ (Here, glycerol was used as the matrix.)

Example 4

Preparation of 4-(3,4-Dihydroxyphenyl)-3-buten-2-one [Compound (8)]

The same procedures as in Preparation Example 1 were carried out using 1 mL of acetone (manufactured by Nakalai Tesque) and 1 g (7.2 mmol) of 3,4-dihydroxy benzaldehyde as starting materials, to give 180 mg of a compound (8) (yield: 14%). The determination results of the NMR spectrum and the mass spectrum are shown below.

$^1$H-NMR: δ 2.26 (3H, s, -Me), 6.47 (1H, d, $J_{\alpha,\beta}$ 16 Hz, H-α), 6.76 (1H, d, $J_{5,6}$ 8 Hz, H-5), 7.00 (1H, dd, $J_{2,6}$ 2 Hz, H-6), 7.05 (1H, d, H-2), 7.43 (1H, d, H-β)

Figure 4:
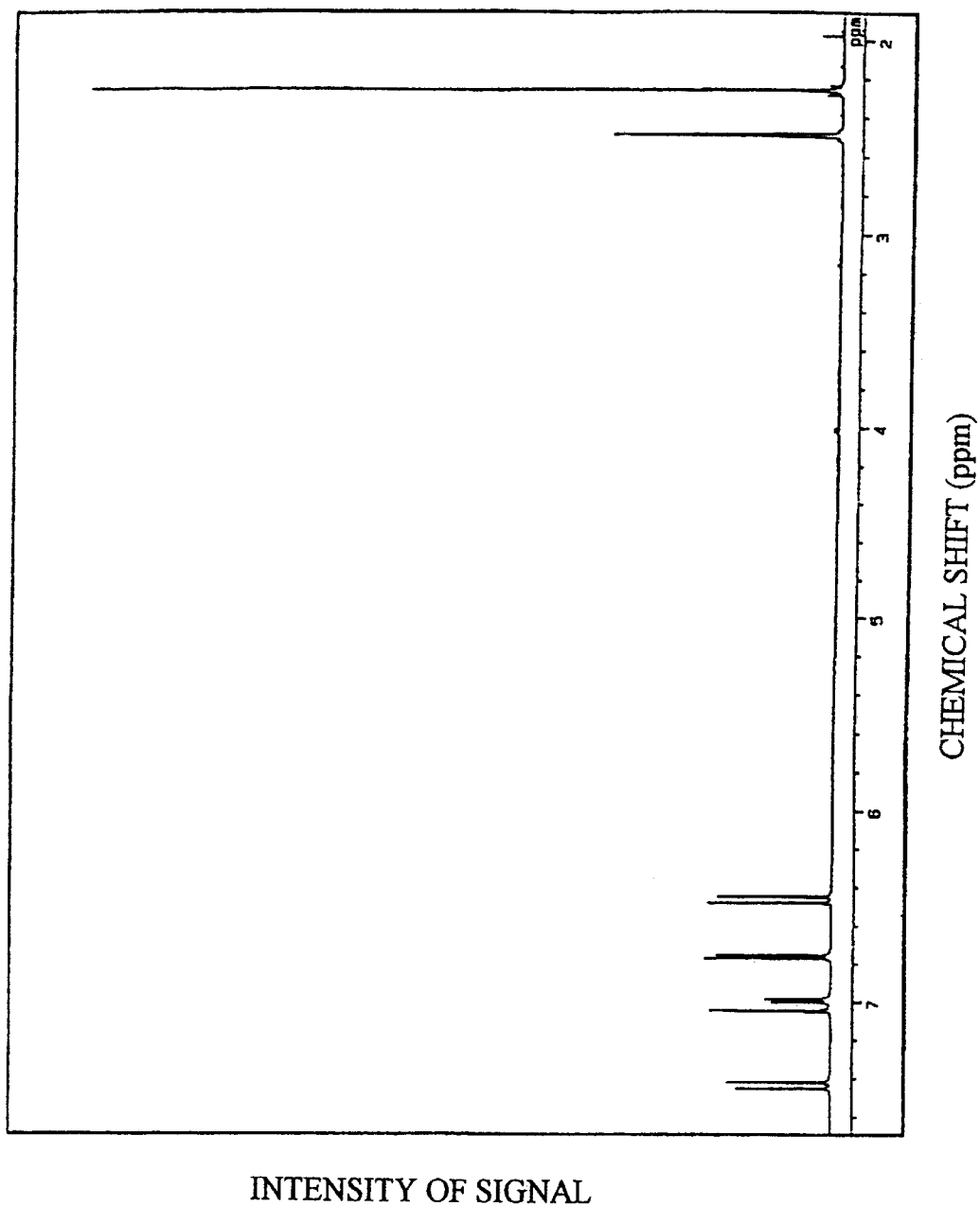
FIG. 4 is a graph showing $^1$H-NMR spectrum of a compound (8).

Here, the sample was dissolved in deuterium dimethyl sulfoxide, and the value of the chemical shift of the residual dimethyl sulfoxide was expressed as 2.49 ppm. FIG. 4 shows the $^1$H-NMR spectrum of the compound (8). In FIG. 4, the axis of abscissas is the value of chemical shift (ppm), and the axis of ordinates is the intensity of signal.

FAB-MS: m/z 179 (M+H)$^+$ (Here, glycerol was used as the matrix.)

Example 5

Preparation of 1-Adamantyl-3-(3,4-dihydroxyphenyl)-2-propen-1-one [Compound (9)]

The same procedures as in Preparation Example 1 were carried out using 640 mg (3.6 mmol) of 1-adamantyl methyl ketone (manufactured by Sigma) and 500 g (3.6 mmol) of 3,4-dihydroxy benzaldehyde as starting materials, to give 500 mg of a compound (9) (yield: 46%). The determination results of the NMR spectrum and the mass spectrum are shown below.

$^1$H-NMR: δ 1.65-2.04 (15H, m, -adamantyl), 6.74 (1H, d, $J_{5,6}$ 8 Hz, H-5), 7.00 (1H, dd, $J_{2,6}$ 2 Hz, H-6), 7.11 (1H, d, $J_{\alpha,\beta}$ 16 Hz, H-α), 7.13 (1H, d, H-2), 7.36 (1H, d, H-β)

Figure 5:
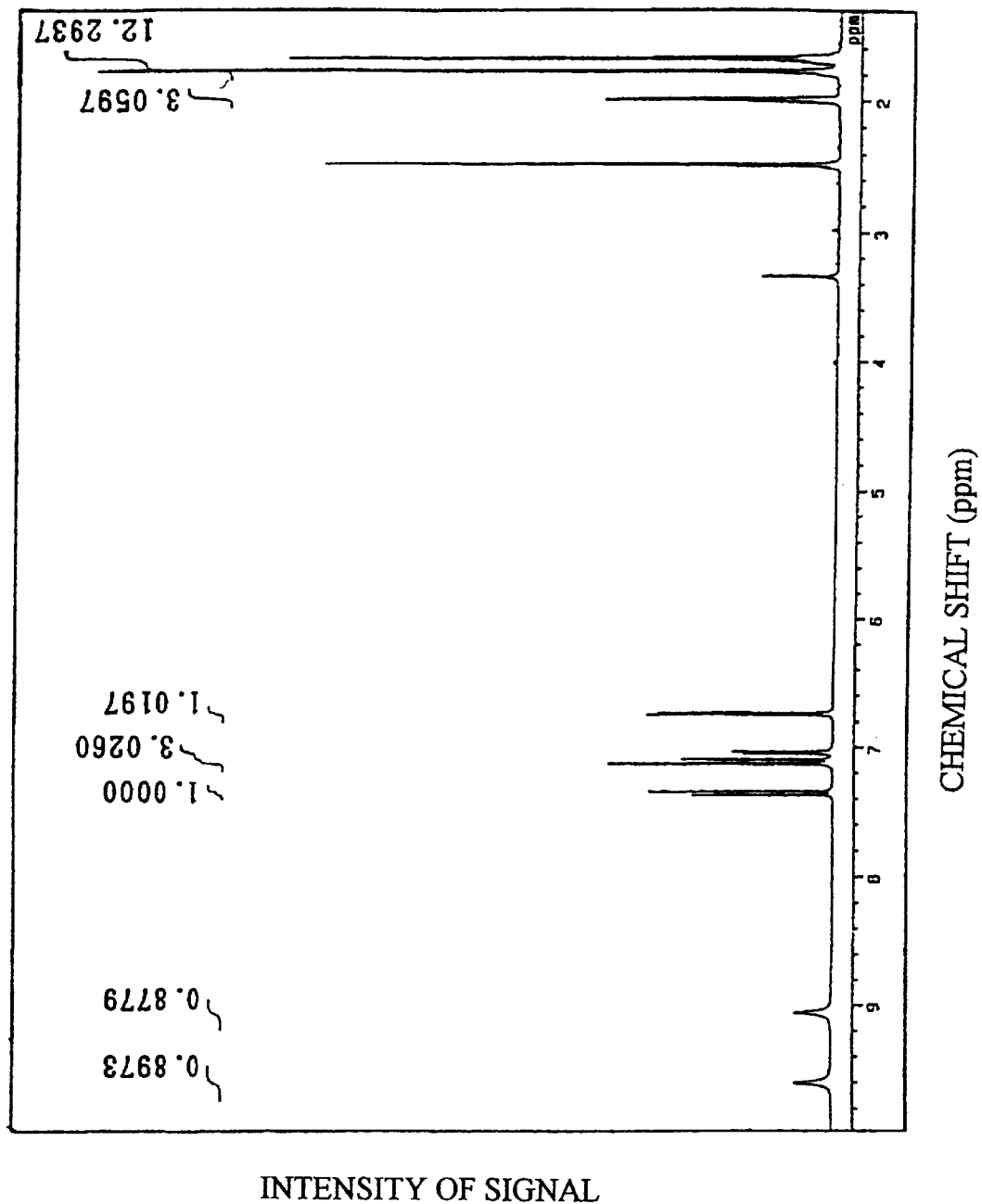
FIG. 5 is a graph showing $^1$H-NMR spectrum of a compound (9).

Here, the sample was dissolved in deuterium dimethyl sulfoxide, and the value of the chemical shift of the residual dimethyl sulfoxide was expressed as 2.49 ppm. FIG. 5 shows the $^1$H-NMR spectrum of the compound (9). In FIG. 5, the axis of abscissas is the value of chemical shift (ppm), and the axis of ordinates is the intensity of signal.

FAB-MS: m/z 299 (M+H)$^+$ (Here, glycerol was used as the matrix.)

Example 6

Preparation of Dihydrobutein [Compound (10)]

Two-hundred milligrams (0.74 mmol) of the compound (13) prepared in Preparation Example 1 was dissolved in 15 mL of methanol. The resulting mixture was stirred at room temperature for 1.5 hours in the presence of 200 mg of palladium (manufactured by Nakalai Tesque), with passing hydrogen gas. The reaction solution was filtrated, and concentrated under reduced pressure. Thereafter, the concentrate was subjected to silica chromatography using a developing solvent of chloroform:methanol=15:1, thereby giving 130 mg of a compound (10) (yield: 65%). The determination results of the NMR spectrum and the mass spectrum are shown below.

$^1$H-NMR: δ 2.74 (1H, t, $J_{\alpha,\beta}$ 7.5 Hz, H-β), 3.16 (1H, t, H-α), 6.23 (1H, d, $J_{3',5'}$ 2.5 Hz, H-3'), 6.34 (1H, dd, $J_{5',6'}$ 9 Hz, H-5'), 6.48 (1H, dd, $J_{5,6}$ 9, $J_{2,6}$ 2 Hz, H-6), 6.60 (1H, d, H-5), 6.61 (1H, d, H-2), 7.77 (1H, d, H-6')

Figure 6:
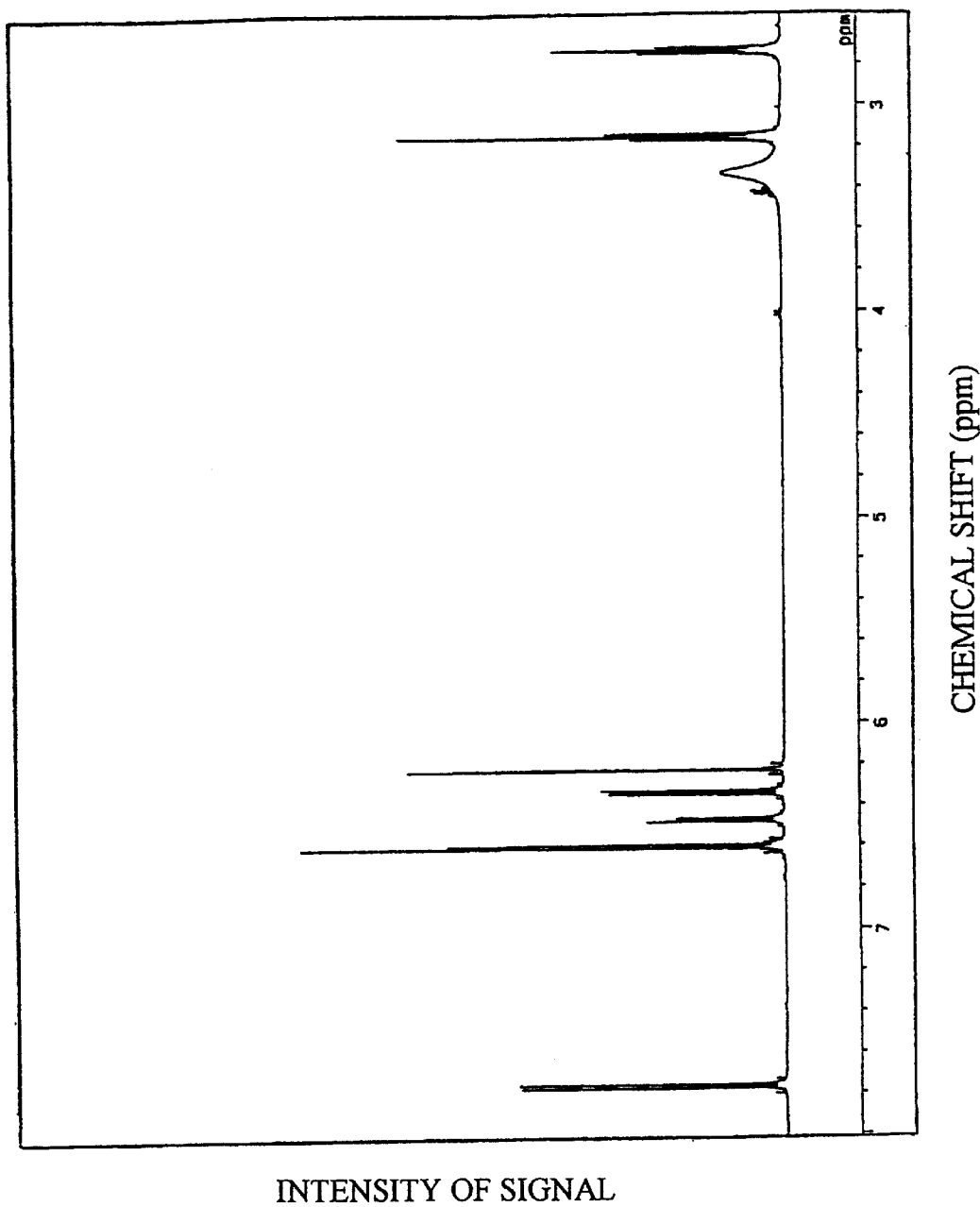
FIG. 6 is a graph showing $^1$H-NMR spectrum of a compound (10).

Here, the sample was dissolved in deuterium dimethyl sulfoxide, and the value of the chemical shift of the residual dimethyl sulfoxide was expressed as 2.49 ppm. FIG. 6 shows the $^1$H-NMR spectrum of the compound (10). In FIG. 6, the axis of abscissas is the value of chemical shift (ppm), and the axis of ordinates is the intensity of signal.

FAB-MS: m/z 275 (M+H)$^+$ (Here, glycerol was used as the matrix.)

Example 7

Preparation of 1-Adamantyl-4-(3,4-dihydroxyphenyl)-3-buten-1-one [Compound (11)]

Nine-hundred milligrams (1.8 mmol) of a compound (12) prepared in Example 8 described below was acetylated in the same manner as in Example 1 [Preparation of the compound (5)]. Thereafter, the resulting compound was dissolved in 40 mL of dichloromethane, and 4 mmol of 1,8-diazabicyclo(5,4,0)-7-undecene (DBU) was added thereto, to carry out the reaction at room temperature for 2 hours. The reaction solution was washed with 10% aqueous citric acid, and dried. Thereafter, the dried product was concentrated to dryness, and the concentrate was subjected to silica chromatography using a developing solvent of hexane:ethyl acetate=5:1, thereby giving the THP form of a compound (11). The THP form of the compound (11) was dissolved in 10 mL of methanol, and 40 g (0.157 mol) of sulfosalicylic acid dehydrate was added thereto. The resulting mixture was stirred at room temperature for 3 hours. The reaction solution was diluted with ethyl acetate, and thereafter washed with saturated aqueous sodium chloride. The resulting solution was dried over anhydrous magnesium sulfate, and concentrated under reduced pressure. Two-hundred and twenty milligrams of the compound (11) was recrystallized from the concentrate with hexane and ethyl acetate (yield: 44%). The determination results of the NMR spectrum and the mass spectrum are shown below.

$^1$H-NMR: δ 1.66-2.00 (15H, m, -adamantyl), 3.37 (1H, dd, $J_{\alpha,\alpha'}$ 7, $J_{\alpha,\beta}$ 1 Hz, H-α), 5.93 (1H, dt, $J_{\beta,\delta}$ 11 Hz, H-β), 6.22 (1H, d, H-δ), 6.59 (1H, dd, $J_{2,6}$ 2, $J_{5,6}$ 8 Hz, H-6), 6.63 (1H, d, H-5), 6.75 (1H, d, H-2)

Figure 7:
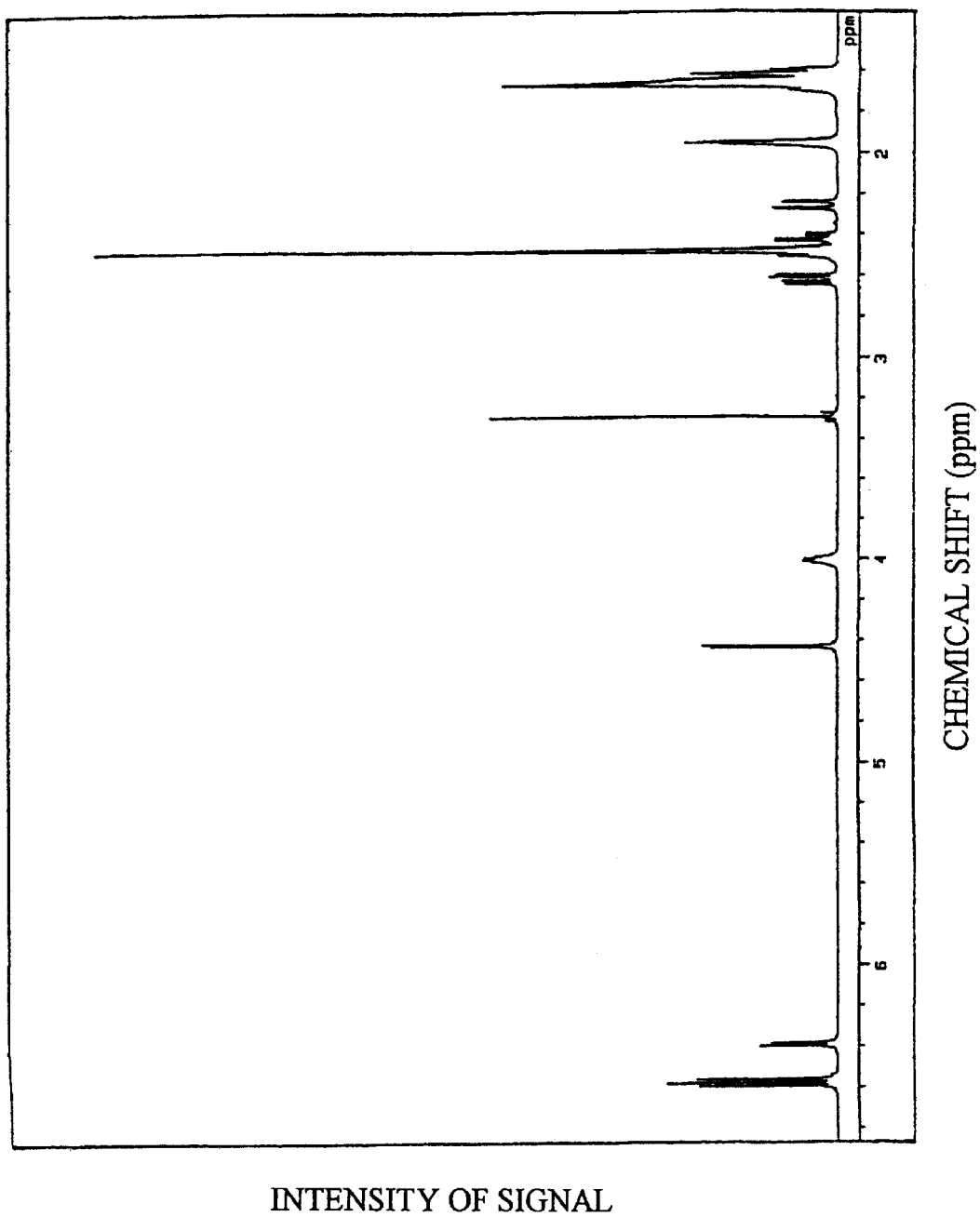
FIG. 7 is a graph showing $^1$H-NMR spectrum of a compound (11).

Here, the sample was dissolved in deuterium dimethyl sulfoxide, and the value of the chemical shift of the residual dimethyl sulfoxide was expressed as 2.49 ppm. FIG. 7 shows the $^1$H-NMR spectrum of the compound (11). In FIG. 7, the axis of abscissas is the value of chemical shift (ppm), and the axis of ordinates is the intensity of signal.

FAB-MS: m/z 313 (M+H)$^+$ (Here, glycerol was used as the matrix.)

Example 8

Preparation of 1-Adamantyl-3-hydroxy-4-(3,4-Dihydroxyphenyl)butan-1-one [Compound (12)]

One milliliter of a 1.6 M butyl lithium hexane solution (manufactured by Nakalai Tesque) was gradually added to 224 μL (1.6 mmol) of diisopropylamine (manufactured by Wako Pure Chemical Industries) in 2 mL of tetrahydrofuran (THF) with ice cooling under an argon gas stream, and the mixture was stirred for 30 minutes. The reaction solution was cooled to −70° C. with methanol/dry ice, a solution of 285 mg (1.6 mmol) of 1-adamantyl methyl ketone in 500 μL of THF was added thereto, and the resulting mixture was stirred for 30 minutes. To this reaction solution was gradually added a solution of 500 mg (1.6 mmol) of the THP form of 3',4'-dihydroxyphenyl acetaldehyde in 500 μL of THF, which was prepared by completely converting 3',4'-dihydroxyphenyl acetic acid (manufactured by Nakalai Tesque) to the THP form, and thereafter reducing the resulting compound with a 1 M DIBAL hexane solution (manufactured by Nakalai Tesque). The resulting mixture was stirred at −70° C. for 10 minutes, and a saturated aqueous ammonium chloride was added to the reaction solution. Subsequently, the organic layer fraction obtained by extraction with an ether was subjected to silica chromatography using a developing solvent of hexane:ethyl acetate=4:1, thereby giving the THP form of the compound (12). The THP form of the compound (12) was dissolved in 10 mL of methanol, and 40 mg (0.157 mmol) of sulfosalicylic acid dehydrate was added thereto. The resulting mixture was stirred at room temperature for 3 hours. The reaction solution was diluted with ethyl acetate, washed with saturated aqueous sodium chloride, dried over anhydrous magnesium sulfate, and concentrated under reduced pressure. Two-hundred and sixty milligrams of the compound (12) was recrystallized from the concentrate with hexane and ethyl acetate (yield: 57%). The determination results of the NMR spectrum and the mass spectrum are shown below.

$^1$H-NMR: δ 1.58-1.98 (15H, m, -adamantyl), 2.25 (1H, dd, $J_{\alpha,\beta}$ 4.5, $J_{\alpha,\alpha'}$ 16.5 Hz, H-α), 2.41 (1H, dd, $J_{\beta,\delta}$ 6.0, $J_{\delta,\delta'}$ 13.5 Hz, H-δ), 2.61 (1H, dd, $J_{\alpha',\beta}$ 4.5 Hz, H-α'), 3.99 (1H, m, H-β), 6.38 (1H, dd, $J_{2,6}$ 2, $J_{5,6}$ 8 Hz, H-6), 6.55 (1H, d, H-2), 6.57 (1H, d, H-2)

Figure 8:
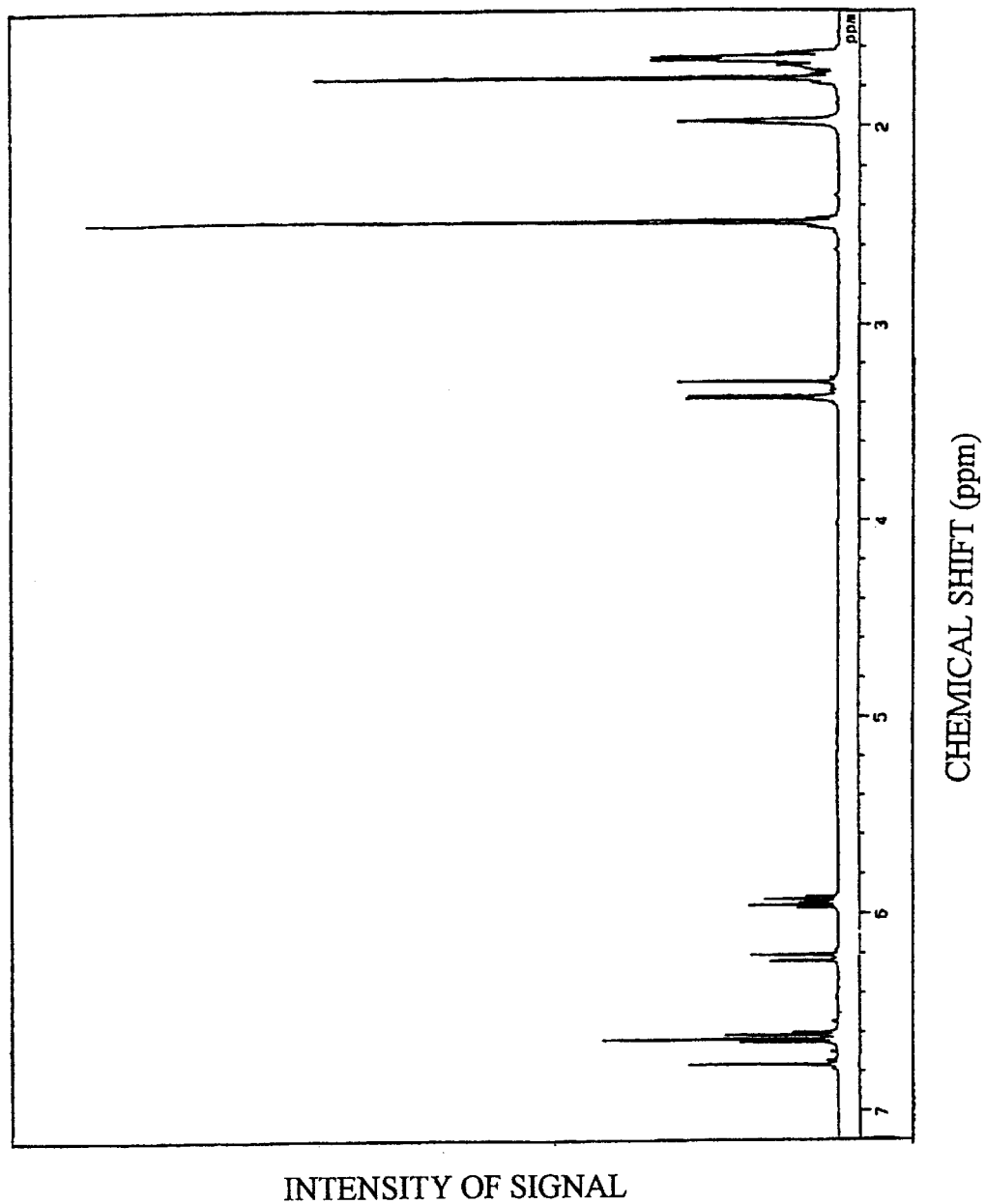
FIG. 8 is a graph showing $^1$H-NMR spectrum of a compound (12).

Here, the sample was dissolved in deuterium dimethyl sulfoxide, and the value of the chemical shift of the residual dimethyl sulfoxide was expressed as 2.49 ppm. FIG. 8 shows the $^1$H-NMR spectrum of the compound (12). In FIG. 8, the axis of abscissas is the value of chemical shift (ppm), and the axis of ordinates is the intensity of signal.

FAB-MS: m/z 331 (M+H)$^+$ (Here, glycerol was used as the matrix.)

Reference Example 1

Study on Method for Assaying Activity of Enhancement for NGF Production Using Caffeic Acid L-M cells (ATCC CCL-1.2) from murine fibroblasts were suspended in an M199 medium (manufactured by ICN) containing 0.5% bactopeptone (manufactured by Gibco BRL) so as to have a concentration of $1.5 \times 10^5$ cells/ml. The suspension was put in a 96-well plate in an amount of 0.1 ml each well, and the cells were aseptically cultured. After culturing the cells for 3 days, the medium was removed therefrom, and exchanged with an M199 medium containing 0.5% bovine serum albumin (manufactured by Sigma). Caffeic acid (manufactured by Sigma, dimethyl suif oxide (DMSO) solution), a substance known to have enhancing activity for NGF production, was added to each well containing the cells, so as to have a final concentration of 0, 50, 100 or 200 μM, and the cells were cultured for 24 hours. One having a caffeic acid concentration of 0 μM was used as a negative control. In addition, the final concentration of DM50 in each well was adjusted to 0.1%. After the termination of the culture, the NGF concentration in the culture medium was determined by an enzyme immunoassay method (NGF Emax Immuno Assay System, manufactured by Promega). The degree of the enhancement for NGF production of caffeic acid at each added amount was expressed in percentage as the enhancement ratio (%) on the basis of the NGF concentration in the cell culture medium at each added amount, when the NGF concentration in the cell culture medium of the negative control was defined as 100%. The results are shown in Table 3. The experiment was carried out twice, and an average value was taken. It was shown that the enhancing activity for NGF production of caffeic acid could be assayed by this method. In addition, it was also shown from this Reference Example that caffeic acid enhanced NGF production in a concentration-dependent manner.

TABLE 3

| Added Amount (μM)       | 0   | 50   | 100 | 200 |
|-------------------------|-----|------|-----|-----|
| Enhancement Ratio (%)   | 100 | 89.7 | 150 | 349 |

Here, the NGF concentration in the negative control was 0.14278 ng/ml.

Example 9

Enhancement for NGF Production by Compound (13)

The enhancing activity for NGF production of the compound (13) (manufactured by Funakoshi) was assayed in the same manner as in Reference Example 1. The compound (13) was added so as to have a final concentration of 0, 0.5, 1, 2, 5, 10, 20 or 50 μM. The results are shown in Table 4. It was shown that the compound (13) enhanced NGF production in the L-M cells in a concentration-dependent manner, exhibited a high enhancing activity for NGF production, and had a broad range of concentration effective for its action.

TABLE 4

| Added Amount (μM)     | 0   | 0.5 | 1   | 2    | 5    | 10   | 20   | 50   |
|-----------------------|-----|-----|-----|------|------|------|------|------|
| Enhancement Ratio (%) | 100 | 120 | 462 | 1107 | 2100 | 3686 | 3927 | 1743 |

Here, the NGF concentration in the negative control was 0.07091 ng/ml.

Example 10

Enhancement for NGF Production by Compound (14)

The enhancing activity for NGF production of a compound (14) (manufactured by Sigma) was assayed in the same manner as in Reference Example 1. The compound (14) was added so as to have a final concentration of 0, 50, 100 or 200 μM. The results are shown in Table 5. It was shown that the compound (14) enhanced NGF production in the L-M cells in a concentration-dependent manner, exhibited a high enhancing activity for NGF production, and had a broad range of concentration effective for its action.

TABLE 5

| Added Amount (μM) | 0 | 50 | 100 | 200 |
|---|---|---|---|---|
| Enhancement Ratio (%) | 100 | 310 | 550 | 1884 |

Here, the NGF concentration in the negative control was 0.07091 ng/ml.

Example 11

Enhancement for NGF Production by Compound (15)

The enhancing activity for NGF production of a compound (15) (manufactured by Sigma) was assayed in the same manner as in Reference Example 1. The compound (15) was added so as to have a final concentration of 0, 12.5, 25 or 50 μM. The results are shown in Table 6. It was shown that the compound (15) enhanced NGF production in the L-M cells in a concentration-dependent manner, exhibited a high enhancing activity for NGF production, and had a broad range of concentration effective for its action.

TABLE 6

| Added Amount (μM) | 0 | 12.5 | 25 | 50 |
|---|---|---|---|---|
| Enhancement Ratio (%) | 100 | 236 | 263 | 320 |

Here, the NGF concentration in the negative control was 0.14278 ng/ml.

Example 12

Enhancement for NGF Production by Compound (16)

The enhancing activity for NGF production of a compound (16) (manufactured by Wako Pure Chemical Industries) was assayed in the same manner as in Reference Example 1. The compound (16) was added so as to have a final concentration of 0, 25, 50 or 100 μM. The results are shown in Table 7. It was shown that the compound (16) enhanced NGF production in the L-M cells in a concentration-dependent manner, exhibited a high enhancing activity for NGF production, and had a broad range of concentration effective for its action.

TABLE 7

| Added Amount (μM) | 0 | 25 | 50 | 100 |
|---|---|---|---|---|
| Enhancement Ratio (%) | 100 | 114 | 116 | 261 |

Here, the NGF concentration in the negative control was 0.14278 ng/ml.

Example 13

Enhancement for NGF Production by Compounds (5) to (12) and (17) to (25)

The enhancing activity for NGF production of each of the compounds (5) to (12), (17) to (22), (24) and (25) prepared in Preparation Examples 2 to 9 and Examples 1 to 8, and the compound (23) (rosemarinic acid; manufactured by Funakoshi), or caffeic acid (CA), 4-methylcatechol (4MC) and epinephrine (EN), substances conventionally known to enhance NGF production was assayed in the same manner as in Reference Example 1. Each of the compounds was added so as to have a final concentration as shown in Tables 8 to 10. In addition, the time period for cell culture after the addition of the compound was 20 hours. The results are shown in Tables 8 to 10. A negative control was set for every test of each compound. Each experiment was carried out twice, and an average value was taken.

TABLE 8

| | NC (ng/ml) | Added Amount (μM) | | | | | | | |
|---|---|---|---|---|---|---|---|---|---|
| | | 0 | 3.125 | 6.25 | 12.5 | 25 | 50 | 100 | 200 |
| | | Enhancement Ratio (%) | | | | | | | |
| CA | 0.179 | 100 | N.T. | N.T. | N.T. | N.T. | 165.1 | 169.9 | 200.5 |
| 4MC | 0.239 | 100 | N.T. | N.T. | 143.0 | 312.9 | 1047.7 | N.T. | N.T. |
| EN | 0.202 | 100 | N.T. | N.T. | N.T. | N.T. | 137.2 | 218.0 | 255.0 |
| Compound (5) | 0.179 | 100 | N.T. | 684.5 | 1330.1 | 1659.5 | N.T. | N.T. | N.T. |
| Compound (6) | 0.167 | 100 | N.T. | 762.7 | 864.3 | 1280.3 | N.T. | N.T. | N.T. |
| Compound (7) | 0.2 | 100 | N.T. | 358.9 | 410.2 | 899.3 | N.T. | N.T. | N.T. |
| Compound (8) | 0.181 | 100 | N.T. | N.T. | N.T. | N.T. | 374.8 | 676.2 | 2198.0 |
| Compound (9) | 0.181 | 100 | 205.6 | 549.6 | 810.3 | N.T. | N.T. | N.T. | N.T. |
| Compound (10) | 0.167 | 100 | N.T. | 174.1 | 333.2 | 839.3 | N.T. | N.T. | N.T. |
| Compound (12) | 0.181 | 100 | 107.6 | 363.7 | 966.5 | 908.3 | 1111.7 | N.T. | N.T. |
| Compound (17) | 0.179 | 100 | N.T. | N.T. | 194.6 | 598.1 | 1101.1 | N.T. | N.T. |
| Compound (18) | 0.2 | 100 | N.T. | 471.1 | 476.0 | 873.6 | N.T. | N.T. | N.T. |

TABLE 8-continued

| | | Added Amount (μM) | | | | | | | |
|---|---|---|---|---|---|---|---|---|---|
| | NC (ng/ml) | 0 | 3.125 | 6.25 | 12.5 | 25 | 50 | 100 | 200 |
| | | Enhancement Ratio (%) | | | | | | | |
| Compound (19) | 0.212 | 100 | N.T. | N.T. | 268.8 | 312.5 | 844.5 | N.T. | N.T. |
| Compound (20) | 0.2 | 100 | N.T. | N.T. | 346.1 | 482.4 | 692.4 | N.T. | N.T. |
| Compound (21) | 0.212 | 100 | N.T. | N.T. | N.T. | 222.7 | 228.8 | 501.5 | N.T. |
| Compound (22) | 0.167 | 100 | N.T. | N.T. | N.T. | N.T. | 123.8 | 130.3 | 242.3 |
| Compound (23) | 0.239 | 100 | N.T. | N.T. | N.T. | N.T. | N.T. | 110.9 | 131.1 |
| Compound (24) | 0.199 | 100 | N.T. | N.T. | N.T. | 126.1 | 202.6 | 265.7 | N.T. |

TABLE 9

| | | Added Amount (μM) | |
|---|---|---|---|
| | NC (ng/ml) | 0 | 0.781 | 1.563 |
| | | Enhancement Ratio (%) | |
| Compound (11) | 0.181 | 100 | 775.2 | 865.8 |

TABLE 10

| | | Added Amount (μM) | | | |
|---|---|---|---|---|---|
| | NC (ng/ml) | 0 | 31.25 | 62.5 | 125 | 250 |
| | | Enhancement Ratio (%) | | | |
| Compound (25) | 0.325 | 100 | 160.6 | 183.6 | 273.6 | 495.3 |

Here, NC in the Tables represents a NGF concentration in the negative control. In addition, N.T. indicates that no test was carried out.

It was shown from these results that the compounds (5) to (12) and (17) to (25) used in the present invention are more useful than caffeic acid, 4-methylcatechol and epinephrine, substances conventionally known to enhance NGF production, in terms of strength of the enhancing activity for NGF production, or the breadth in the concentration range in which the enhancing activity for NGF production is exhibited.

Example 14

(1) L-M cells (ATCC CCL-1.2) from murine fibroblasts were suspended in an M199 medium (manufactured by ICN) containing 0.5% bactopeptone (manufactured by Gibco) so as to have a concentration of $1.5 \times 10^5$ cells/ml. The suspension was put in a 96-well plate in an amount of 0.1 ml each well, and the cells were aseptically cultured. After culturing the cells for 3 days, the medium was removed therefrom, and exchanged with an M199 medium containing 0.5% bovine serum albumin (manufactured by Sigma). Thereto was added an yellow pigment (powder Sun Yellow No. 2, manufactured by San-Ei Gen F.F.I.) obtained by extraction from flower of Carthamus tinctorius LINNE) as the sample so as to have a final concentration of 0, 1.25, 2.5 or 5 mg/ml, and the cells were cultured for 20 hours. After the termination of the culture, the NGF concentration in the culture medium was assayed by an enzyme immunoassay method (NGF Emax Immuno Assay System, manufactured by Promega). The degree of the enhancement for NGF production was expressed in the percentage as an enhancement ratio (%), when the NGF concentration in the cell culture medium with no addition of the sample as the negative control was defined as 100%. The experiment was carried out twice, and an average value was taken. As a result, the yellow pigment from Carthamus tinctorius LINNE enhanced NGF production of the L-M cells in a concentration-dependent manner. The results are shown in Table 11.

TABLE 11

| Added Amount (mg/ml) | Enhancement Ratio (%) |
|---|---|
| 0 | 100 |
| 1.25 | 277.6 |
| 2.5 | 441.3 |
| 5 | 808.4 |

Here, the NGF concentration in the negative control was 0.507 ng/ml.

(2) The active component in the yellow pigment from Carthamus tinctorius LINNE described in item (1) of Example 14 was purified and isolated by reverse-phase chromatography. The conditions are shown below. The column used was TSK gel ODS-80Ts (diameter: 21.5 mm, length: 30 cm, manufactured by Tosoh Corporation). The elution ratio of Solvent A (0.1% aqueous trifluoroacetic acid) and Solvent B (mixture of distilled water and acetonitrile in a volume ratio of 1:1, containing 0.1% trifluoroacetic acid) was such that the ratio of Solvent B was increased linearly from 0 to 100% from 0 to 50 minutes, the ratio of Solvent B was retained at 100% for the subsequent 15 minutes, and the ratio of Solvent B was finally decreased to 0% and retained thereat for 15 minutes. The elution rate was 5 ml/minute, and the detection was carried out at 215 nm. A fraction was collected every 3 minutes, and the enhancing activity for NGF production was determined for each fraction in the same manner as in Example 13. As a result, it was shown that the fraction including peaks detected at retention time of 32.5 minutes and 41.8 minutes had the activity. The fraction having a retention time of 32.5 minutes was analyzed by mass spectrum. As a result, a signal corresponding to a molecular weight of 613 was detected. Further, as a result of analyses by the $^1$H-NMR spectrum (FIG. 9) and the $^{13}$C-NMR spectrum, the active component was identified as safflomin A (molecular weight: 612.53), a compound (27) represented by the formula (27).

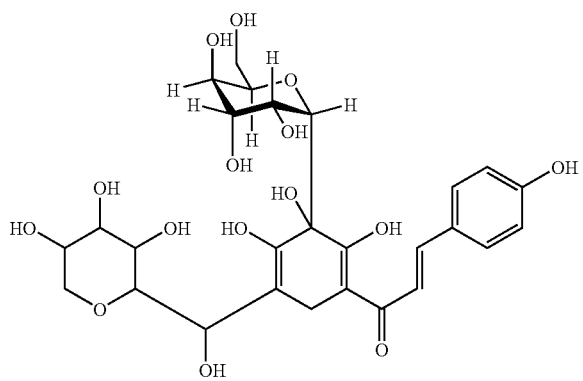

(27)

The enhancing activity for NGF production of the purified safflomin A thus obtained was determined in the same manner as in Example 13. The purified safflomin A was added so as to have a final concentration of 0 or 2.5 mg/ml. As a result, the purified safflomin A enhanced NGF production of the L-M cells. The results for safflomin A are shown in Table 12, and the results for the substance contained in the fraction having a retention time of 41.8 minutes are shown in Table 13 (The amounts of the substance added are shown in Table 13).

TABLE 12

| Added Amount (mg/ml) | Enhancement Ratio (%) |
|---|---|
| 0 | 100 |
| 2.5 | 130.7 |

Here, the NGF concentration in the negative control was 0.739 ng/ml.

TABLE 13

| Added Amount (mg/ml) | Enhancement Ratio (%) |
|---|---|
| 0 | 100 |
| 1.25 | 350.7 |
| 2.5 | 643.4 |

Here, the NGF concentration in the negative control was 0.736 ng/ml.

Example 15

Enhancement for NGF Production by Xanthohumol

The enhancing activity for NGF production of xanthohumol prepared in Preparation Example 10 was assayed in the same manner as in Example 13. Xanthohumol was added so as to have a final concentration of 0, 15.6, 31.3, 62.5 or 125 µM. The results are shown in Table 14. It was shown that xanthohumol enhanced NGF production in the L-M cells in a concentration-dependent manner, exhibited a high enhancing activity for NGF production, and had a broad range of concentration effective for its action.

TABLE 14

| Added Amount (µM) | Enhancement Ratio (%) |
|---|---|
| 0 | 100 |
| 15.6 | 160.3 |
| 31.3 | 212.1 |
| 62.5 | 473.2 |
| 125 | 897.1 |

Here, the NGF concentration in the negative control was 0.0575 ng/ml.

Example 16

(1) Enhancement for NGF Production by Myricetin

L-M cells (ATCC CCL-1.2) from rat fibroblasts were suspended in an M199 medium (manufactured by ICN) containing 0.5% bactopeptone (manufactured by Gibco BRL) so as to have a concentration of $1.5 \times 10^5$ cells/ml. The suspension was put in a 96-well plate in an amount of 0.1 ml each well, and the cells were aseptically cultured. After culturing the cells for 3 days, the medium was removed therefrom, and exchanged with an M199 medium containing 0.5% bovine serum albumin (manufactured by Sigma).

Myricetin (manufactured by Sigma) was added to each well containing the cells so as to have a final concentration of 0, 31.3, 62.5, 125 or 250 µM, and the cells were cultured for 24 hours. As the negative control, that with addition of distilled water was used. After the termination of the culture, the NGF concentration in the culture medium was assayed by an enzyme immunoassay method (NGF Emax Immuno Assay System, manufactured by Promega). The degree of the enhancement for NGF production at each added amount was expressed in percentage as the enhancement ratio (%) on the basis of the NGF concentration in the cell culture medium at each added amount when the NGF concentration in the cell culture medium of the negative control was defined as 100%. The results are shown in Table 15. The experiment was carried out twice, and an average value was taken. Myricetin enhanced NGF production in the L-M cells in a concentration-dependent manner.

TABLE 15

| Added Amount (µM) | 0 | 31.3 | 62.5 | 125 | 250 |
|---|---|---|---|---|---|
| Enhancement Ratio (%) | 100 | 111 | 137 | 307 | 397 |

Here, the NGF concentration in the negative control was 0.038 ng/ml.

(2) Enhancement for NGF Production by Quercetin

The enhancing activity for NGF production of quercetin (manufactured by Sigma) was assayed in the same manner as in item (1) of Example 16. Quercetin was added so as to have a final concentration of 0, 31.3, 62.5, 125 or 250 µM. The results are shown in Table 16. Quercetin enhanced NGF production in the L-M cells in a concentration-dependent manner.

TABLE 16

| Added Amount (μM) | 0 | 31.3 | 62.5 | 125 | 250 |
|---|---|---|---|---|---|
| Enhancement Ratio (%) | 100 | 122 | 108 | 173 | 219 |

Here, the NGF concentration in the negative control was 0.053 ng/ml.

(3) Enhancement for NGF Production by Myricitrin

The enhancing activity for NGF production of myricitrin (manufactured by Funakoshi) was assayed in the same manner as in item (1) of Example 16. Myricitrin was added so as to have a final concentration of 0, 31.3, 62.5, 125 or 250 μM. The results are shown in Table 17. Myricitrin enhanced NGF production in the L-M cells in a concentration-dependent manner.

TABLE 17

| Added Amount (μM) | 0 | 31.3 | 62.5 | 125 | 250 |
|---|---|---|---|---|---|
| Enhancement Ratio (%) | 100 | 105 | 159 | 294 | 304 |

Here, the NGF concentration in the negative control was 0.053 ng/ml.

(4) Enhancement for NGF Production by Quercitrin

The enhancing activity for NGF production of quercitrin (manufactured by Sigma) was assayed in the same manner as in item (1) of Example 16. Quercitrin was added so as to have a final concentration of 0, 31.3, 62.5, 125 or 250 μM. The results are shown in Table 18. Quercitrin enhanced NGF production in the L-M cells in a concentration-dependent manner.

TABLE 18

| Added Amount (μM) | 0 | 31.3 | 62.5 | 125 | 250 |
|---|---|---|---|---|---|
| Enhancement Ratio (%) | 100 | 122 | 140 | 193 | 207 |

Here, the NGF concentration in the negative control was 0.053 ng/ml.

Example 17

Male SD rats were purchased from Nippon SLC, and used for an experiment at 5 weeks old after preliminary rearing. Streptozotocin (manufactured by Nakalai Tesque) was administered intraperitoneally to the rats at a dose of 100 mg/kg body weight to induce diabetes. The rats were divided into groups according to the blood sugar level after 5 days from the administration of streptozotocin. Next, a solution prepared by dissolving butein [compound (13)] in physiological saline was administered intraperitoneally to the rats at a dose of 100 μg per 1 kg body weight. In the control group, physiological saline alone was administered in the same manner. The rats were administered for consecutive days, and sciatic nerves (about 35 mg) were enucleated after 4 weeks from the beginning of administration. The enucleated sciatic nerves were homogenized, and NGF was extracted. The content of NGF was assayed by an enzyme immunoassay method (NGF Emax Immuno Assay System, manufactured by Promega).

The results are shown in Table 19. The numerical figures in the table are expressed by an average value±standard error of 6 cases. In addition, the asterisk * means that the group has a significant difference at a significance level of 5% or less as compared to the control group according to Student-t test. In other words, the content of NGF in the nerves was increased in the group administered with butein as compared to that of the control group. As described above, it was clarified that the NGF production was enhanced by the administration of butein to a living body.

TABLE 19

| | Content of NGF (pg/Sciatic Nerves) |
|---|---|
| Group Administered with Butein (N = 6) | 187.7 ± 26.4* |
| Control Group (N = 6) | 119.2 ± 11.7 |

Average Value ± Standard Error

Example 18

(1) L-M cells (ATCC CCL-1.2) from murine fibroblasts were suspended in an M199 medium (manufactured by ICN) containing 0.5% bactopeptone (manufactured by Gibco) so as to have a concentration of $2.5 \times 10^5$ cells/ml. The suspension was put in a 6-well plate in an amount of 2 ml each well, and the cells were aseptically cultured. After culturing the cells for 3 days, the medium was removed therefrom, and exchanged with 1 ml of an M199 medium containing 0.5% bovine serum albumin (manufactured by Sigma). A solution prepared by dissolving butein [compound (13)] in dimethyl sulfoxide was added thereto so as to have a final concentration of 20 μM (final concentration of DMSO: 0.1%), and the cells were cultured for 20 hours. After the termination of the culture, culture supernatant was collected, and an equal volume of DME medium (manufactured by Bio Whittaker) containing 20% fetal bovine serum (manufactured by JRH Bioscience) was added thereto. The resulting solution was passed through a sterilized filter having a pore size of 0.22 μm, to give a butein-treated preparation medium. In addition, similar procedures were carried out for the culture supernatant in which DMSO alone was added in place of butein so as to have a final concentration of 0.1%, to give a control preparation medium.

(2) The biochemical activity of NGF contained in the butein-treated preparation medium and the control preparation medium prepared in item (1) of Example 18 was evaluated by the following method.

First, PC-12 cells (ATCC CRL-1721) from rat pheochromocytom of the adrenal gland were previously suspended in a DME medium containing 10% fetal bovine serum so as to have a concentration of $2.0 \times 10^4$ cells/ml. The suspension was put in a collagen-coated 96-well plate in an amount of 0.1 ml each well, and the cells were aseptically cultured for 24 hours. Next, a series of two-fold dilutions (stock solution, ½ dilution, ¼ dilution, ⅛ dilution, ¹⁄₁₆ dilution and ¹⁄₃₂ dilution) were prepared for the butein-treated preparation medium and the control preparation medium, with a mixed medium (hereinafter referred to as medium for assay) prepared by mixing equal volumes of an M199 medium containing 0.5% bovine serum albumin and a DME medium containing 20% fetal bovine serum. The medium was removed from the cultured PC-12 cells, and 100 μl of each of the above-mentioned stepwise dilutions of the butein-treated preparation medium and the control preparation medium was added to the cells, and the cells were aseptically cultured for 48 hours. Here, as comparison, the medium for assay alone was added to the cells in place of the preparation medium in an amount of 100 μl, and the cells were aseptically cultured for 48 hours. After the termination of the culture, photographs (magnification: ×100) of the cells were taken under observation with a microscope (manufactured by OLYMPUS OPTICAL COMPANY LIMITED), with randomly selecting the scope. The number of axon extension-positive PC-12 cells was counted 300 to 500 cells in the photograph, and the ratio of axon extension (%) was calculated by the following equation.

Ratio of Axon Extension (%)=Number of Axon Extension-Positive Cells(−)÷ Total Number of Cells(−)×100

Here, the axon extension-positive cells are defined as cells of which axon has a length longer than the maximum diameter of the cell. The results of the ratio of axon extension (%) as calculated for the butein-treated preparation medium and the control preparation medium are shown in Table 20. The experiment was carried out three times, and an average value was taken. The butein-treated preparation medium showed high activity of axon extension as compared to that of the control preparation medium.

TABLE 20

| | Ratio of Axon Extension (%) | |
|---|---|---|
| Dilution | Butein-Treated Preparation Medium | Control Preparation Medium |
| Stock solution | 64.1 | 33.5 |
| ½ Dilution | 60.1 | 21.7 |
| ¼ Dilution | 42.8 | 11.6 |
| ⅛ Dilution | 38.3 | 10.6 |
| 1/16 Dilution | 27.7 | 8.87 |
| 1/32 Dilution | 21.2 | 4.02 |

In the case where the medium for assay alone was added, the ratio of axon extension was 3.66%.

Example 19

Preparation 1 of Therapeutic Agent Injections

I. Butein [compound (13)] was added to physiological saline to have a concentration of 1%, to give an injection.

II. Butein [compound (13)] and glycyrrhizic acid were added to physiological saline to have concentrations of 0.5% and 0.1%, respectively, to give an injection.

Also, an injection was prepared in the same manner as in the above items I and II for each of the compounds (5) to (12) and (14) to (25).

Tablet

III. A tablet containing 100 mg of butein [compound (13)] and an appropriate amount of microcrystalline cellulose was prepared, and covered with a sugar, to give each tablet.

IV. A tablet containing 0.1 mg of butein [compound (13)], 10 mg of dipotassium glycyrrhizate and an appropriate amount of microcrystalline cellulose was prepared, and covered with a sugar, to prepare a tablet.

Also, a tablet was prepared in the same manner as in the above items III and IV for each of the compounds (5) to (12) and (14) to (27).

Example 20

Preparation 2 of Therapeutic Agent Injections

I. Myricetin was added to physiological saline to have a concentration of 1%, to give an injection.

II. Myricetin and glycyrrhizic acid were added to physiological saline to have concentrations of 0.5% and 0.1%, respectively, to give an injection.

Tablet

I. A tablet containing 100 mg of myricetin and an appropriate amount of microcrystalline cellulose was prepared, and covered with a sugar, to give each tablet.

II. A tablet containing 0.1 mg of myricetin, 10 mg of dipotassium glycyrrhizate and an appropriate amount of microcrystalline cellulose was prepared, and covered with a sugar, to give a tablet.

Test Example 1

Toxicity Test

Male SD rats were purchased from Nippon SLC, and used for an experiment from 6 week-old after preliminary rearing. A solution prepared by dissolving butein [compound (13)] in physiological saline was administered intraperitoneally, or a suspension prepared by suspending butein in 0.5% carboxymethylcellulose was given by forced oral administration, to the rats. The concentration of administration was 300 mg (N=3), 10 mg (N=3), 1 mg (N=3) or 0.1 mg (N=3) per 1 kg body weight in the case of intraperitoneal administration, and 1 g (N=2) and 0.1 g (N=3) per 1 kg body weight in the case of forced oral administration. In the control group, each of the solvents alone was administered in the same manner. After the administration, no cases of death, changes in the general conditions, suppression of the increase in the body weight or abnormal findings at the dissection were found in any of the administered groups.

In addition, the compound used as an effective ingredient in the present invention was tested in the same manner by orally administering the compound to $CDF_1$ mice (male, 7-week old, Nippon SLC). As a result, it was confirmed that the compound was non-toxic or low-toxic.

Test Example 2

Toxicity Test

Each of the compounds used in Example 16 was orally administered to mice in the same manner as in Test Example 1 described above. As a result, it was confirmed that each of the compounds was low-toxic.

INDUSTRIAL APPLICABILITY

According to the present invention, there is provided a medicament having an enhancing activity for NGF production, comprising the above-mentioned effective ingredient. The medicament is useful for sustaining homeostasis of a living body as a therapeutic agent or prophylactic agent for a disease that requires enhancement of NGF production. In addition, in the present invention, there is provided an enhancer for NGF production, comprising the above-mentioned effective ingredient. The enhancer is useful for biochemical studies on nerve cell mechanism and screening for drugs for dementia, nerve disorders and the like. Further, in the present invention, there is provided a food, beverage or feed for enhancing NGF production. These foods, beverages or feeds are very useful for ameliorating or preventing a symptom for a disease that requires enhancement of NGF production which is sensitive to the effective ingredient used in the present invention. In addition, in the present invention, there is provided a novel compound having an enhancing action for NGF production.

What is claimed is:

1. A method for enhancing nerve growth factor production, comprising administering to an animal at least one compound selected from the group consisting of the compound represented by the general formula (1):

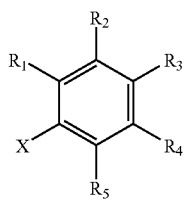

(1)

wherein each of $R_1$, $R_2$, $R_3$, $R_4$ and $R_5$, which may be identical or different, is hydrogen atom, hydroxyl group, an alkoxy group or an acyloxy group; X is a group represented by the following general formula (2):

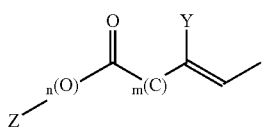

(2)

wherein Z is a substituted or unsubstituted aliphatic group, or aromatic group or aromatic-aliphatic group; Y is a hydrogen atom or hydroxyl group; and each of m and n is 0 or 1; a group represented by the following general formula (3):

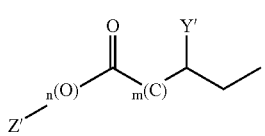

(3)

wherein Z' is hydrogen atom, a substituted or unsubstituted aliphatic group, aromatic group or aromatic-aliphatic group; Y' is a hydrogen atom or hydroxyl group; and each of m and n is 0 or 1; or a group represented by the following general formula (4):

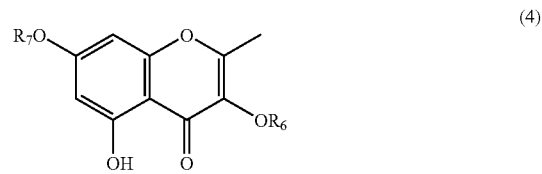

(4)

wherein each of $R_6$ and $R_7$, which may be identical or different, is a hydrogen atom, a sugar residue, or a substituted or unsubstituted aliphatic group, aromatic group or aromatic-aliphatic group; excluding a case where $R_1$, $R_4$ and $R_5$ are all hydrogen atoms, $R_2$ and $R_3$ are all hydroxyl groups, and X is represented by said general formula (2) in said general formula (1), wherein n is 1, m is 0, and Z and Y are hydrogen atom in said general formula (2), and pharmacologically acceptable salts thereof.

2. A food, beverage or feed for enhancing nerve growth factor production, wherein the food, beverage or feed comprises as an effective ingredient at least one compound selected from the group consisting of the compound represented by the general formula (1) and pharmacologically acceptable salts thereof as defined in claim 1.

3. A compound selected from the group consisting of the compounds represented by the following formulas (5), (6) and (9) to (12):

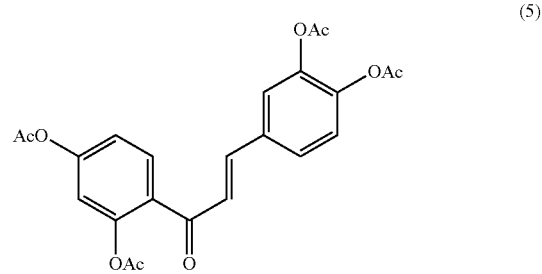

(5)

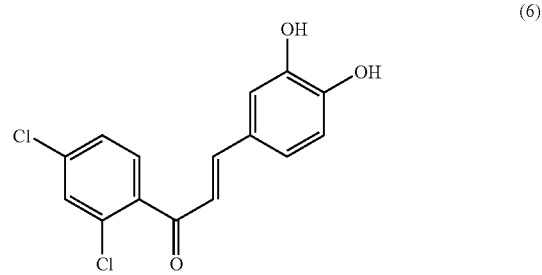

(6)

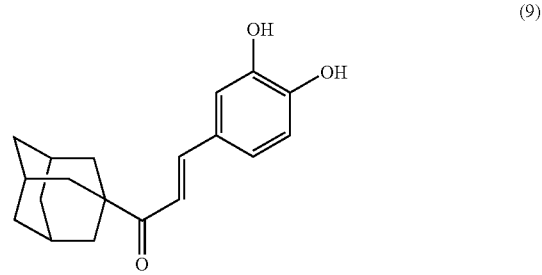

(9)

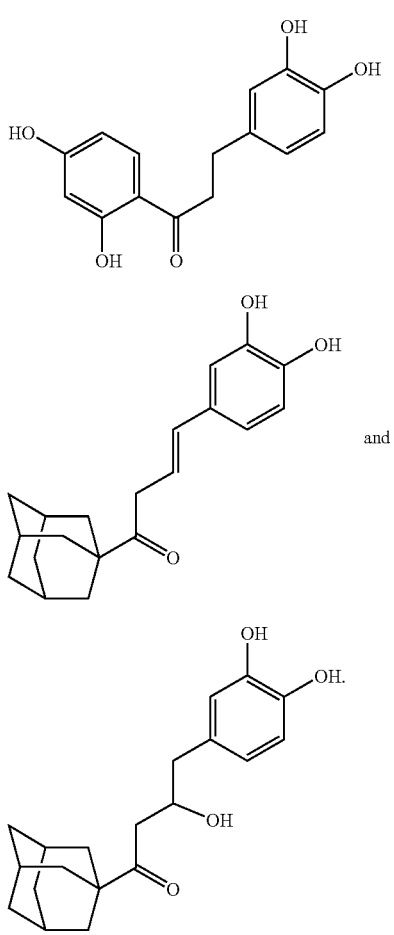

4. A therapeutic composition or prophylactic composition for a disease that requires enhancement of nerve growth factor production, wherein the therapeutic composition or prophylactic composition comprises as an effective ingredient at least one compound selected from the group consisting of the compound represented by the general formula (1) and pharmacologically acceptable salts thereof as defined in claim 1 and wherein Z is 2,4-diacetoxyphenyl group, 2,4-dichlorophenyl group, 2,4-dimethoxyphenyl group, adamantyl group, 2,4-dihydroxyphenyl group, phenylethyl group, 2-oxo-4-(4-hydroxy-3-methoxy-phenyl)-3-butenyl group, 2,5-dihydroxyphenyl group, 3,4-dihydroxyphenyl group, 3,5-dihydroxyphenyl group, 2-hydroxyphenyl group, 2,3,4-trihydroxyphenyl group, 1-carboxy-2-(3,4-dihydroxyphenyl)ethyl group, 3-geranyl-2,4-dihydroxyphenyl group, 2,4-dihydroxy-6-methoxy-3-prenylphenyl group or 3-glucopyranosyl-2,3,4-trihydroxy-5-[(3,4,5,6-tetrahydro-3,4,5-trihydroxy-2H-pyran-2-yl)-hydroxymethyl]-6-oxo-1,4-cyclohexadien-1-yl group, and a pharmaceutically acceptable vehicle therefor.

5. An enhancing composition for nerve growth factor production, wherein the enhancing composition comprises as an effective ingredient at least one compound selected from the group consisting of the compound represented by the general formula (1) and pharmacologically acceptable salts thereof as defined in claim 1, and wherein Z is 2,4-diacetoxyphenyl group, 2,4-dichlorophenyl group, 2,4-dimethoxyphenyl group, adamantyl group, 2,4-dihydroxyphenyl group, phenylethyl group, 2-oxo-4-(4-hydroxy-3-methoxy-phenyl)-3-butenyl group, 2,5-dihydroxyphenyl group, 3,4-dihydroxyphenyl group, 3,5-dihydroxyphenyl group, 2-hydroxyphenyl group, 2,3,4-trihydroxyphenyl group, 1-carboxy-2-(3,4-dihydroxyphenyl)ethyl group, 3-geranyl-2,4-dihydroxyphenyl group, 2,4-dihydroxy-6-methoxy-3-prenylphenyl group or 3-glucopyranosyl-2,3,4-trihydroxy-5-[(3,4,5,6-tetrahydro-3,4,5-trihydroxy-2H-pyran-2-yl)-hydroxymethyl]-6-oxo-1,4-cyclohexadien-1-yl group, and a pharmaceutically acceptable vehicle therefor.

6. The food, beverage or feed according to claim 2, wherein Z is 2,4-diacetoxyphenyl group, 2,4-dichlorophenyl group, 2,4-dimethoxyphenyl group, methyl group, adamantyl group, 2,4-dihydroxyphenyl group, phenylethyl group, 2-oxo-4-(4-hydroxy-3-methoxy-phenyl)-3-butenyl group, 2,5-dihydroxyphenyl group, 3,4-dihydroxyphenyl group, 3,5-dihydroxyphenyl group, 2-hydroxyphenyl group, 2,3,4-trihydroxyphenyl group, 1-carboxy-2-(3,4-dihydroxyphenyl)ethyl group, 3-geranyl-2,4-dihydroxyphenyl group, 2,4-dihydroxy-6-methoxy-3-prenylphenyl group or 3-glucopyranosyl-2,3,4-trihydroxy-5-[(3,4,5,6-tetrahydro-3,4,5-trihydroxy-2H-pyran-2-yl)-hydroxymethyl]-6-oxo-1,4-cyclohexadien-1-yl group.

7. The food, beverage or feed according to claims 2 or 6, wherein the food, beverage or feed is food.

8. The food, beverage or feed according to claims 2 or 6, wherein the food, beverage or feed is beverage.

9. The food, beverage or feed according to claims 2 or 6, wherein the food, beverage or feed is feed.

* * * * *